(12) United States Patent
Allen et al.

(10) Patent No.: US 8,679,187 B2
(45) Date of Patent: Mar. 25, 2014

(54) ACETABULAR CUP ASSEMBLY FOR MULTIPLE BEARING MATERIALS

(75) Inventors: Charles Wayne Allen, Southaven, MS (US); Jason A. Capriotti, Senatobia, MS (US); Michael A. Croxton, Germantown, TN (US); Roger William Frank Ashton, Warwick (GB); Justin M. Waugh, Memphis, TN (US); Jeffrey J. Shea, Memphis, TN (US); Sureshkumar Srinivasan, Collierville, TN (US); William L. Waltersdorff, Hernando, MS (US); Terry W. McLean, Cordova, TN (US)

(73) Assignee: Smith & Nephew, Inc., Memphis, TN (US)

( * ) Notice: Subject to any disclaimer, the term of this patent is extended or adjusted under 35 U.S.C. 154(b) by 472 days.

(21) Appl. No.: 12/293,705

(22) PCT Filed: Oct. 18, 2006

(86) PCT No.: PCT/US2006/060044
§ 371 (c)(1),
(2), (4) Date: Sep. 29, 2010

(87) PCT Pub. No.: WO2007/108848
PCT Pub. Date: Sep. 27, 2007

(65) Prior Publication Data
US 2011/0009975 A1    Jan. 13, 2011

Related U.S. Application Data

(60) Provisional application No. 60/783,937, filed on Mar. 20, 2006.

(51) Int. Cl.
*A61F 2/34*      (2006.01)
(52) U.S. Cl.
USPC .................. 623/22.24; 623/22.21; 623/22.25; 623/22.26
(58) Field of Classification Search
USPC ............................................ 623/22.21–22.32
IPC .......................................................... A61F 2/34
See application file for complete search history.

(56) References Cited

U.S. PATENT DOCUMENTS

| | | | |
|---|---|---|---|
| 3,818,512 A | 6/1974 | Shersher | |
| 3,875,593 A | 4/1975 | Shersher | |

(Continued)

FOREIGN PATENT DOCUMENTS

| | | | |
|---|---|---|---|
| AU | 6761787 A | 7/1987 | |
| CH | 662267 A5 | 9/1987 | |

(Continued)

OTHER PUBLICATIONS

Mathiesen, et al., "Corrosion of Modular Hip Prosthesis", J Bone Joint Surg [Br] 1991; 73-B; 569-75.

(Continued)

*Primary Examiner* — David Isabella
*Assistant Examiner* — Yashita Sharma
(74) *Attorney, Agent, or Firm* — David Chambers

(57) ABSTRACT

A modular acetabular cup assembly (10, 100, 200, 300, 350) for use with multiple bearing liners (32, 110, 212, 310, 354) is disclosed. The acetabular cup assembly includes a shell (12) having a tapered inner wall (28) and two circumferential grooves (24, 26). The shell (12) may be used with polyethylene, ceramic, metal, and other types of liners.

20 Claims, 13 Drawing Sheets

(56) References Cited

U.S. PATENT DOCUMENTS

| | | |
|---|---|---|
| 3,894,297 A | 7/1975 | Mittelmeier et al. |
| 3,903,549 A | 9/1975 | Deyerle |
| 3,922,726 A | 12/1975 | Trentani et al. |
| 3,977,026 A | 8/1976 | Battault |
| 3,982,281 A | 9/1976 | Giliberty |
| D249,957 S | 10/1978 | Eicher et al. |
| 4,179,485 A | 12/1979 | Tritten |
| 4,180,873 A | 1/1980 | Fixel |
| 4,241,463 A | 12/1980 | Khovaylo |
| 4,301,065 A | 11/1981 | Bach et al. |
| 4,318,191 A | 3/1982 | Tepic |
| 4,380,090 A | 4/1983 | Ramos |
| 4,479,271 A | 10/1984 | Bolesky et al. |
| 4,596,580 A | 6/1986 | Weill |
| 4,624,674 A | 11/1986 | Pappas et al. |
| 4,650,491 A | 3/1987 | Parchinski |
| 4,662,891 A | 5/1987 | Noiles |
| 4,666,448 A | 5/1987 | Ganz |
| 4,666,449 A | 5/1987 | Frey et al. |
| 4,666,450 A | 5/1987 | Kenna |
| 4,676,798 A | 6/1987 | Noiles |
| 4,676,799 A | 6/1987 | Legrand |
| 4,678,472 A | 7/1987 | Noiles |
| 4,681,589 A * | 7/1987 | Tronzo ............... 623/22.32 |
| 4,695,282 A | 9/1987 | Forte et al. |
| 4,714,477 A | 12/1987 | Fichera et al. |
| 4,715,860 A | 12/1987 | Amstutz et al. |
| 4,728,335 A | 3/1988 | Jurgutis |
| 4,731,088 A * | 3/1988 | Collier ............... 623/22.13 |
| 4,752,296 A | 6/1988 | Buechel et al. |
| 4,770,658 A | 9/1988 | Geremakis |
| 4,770,659 A | 9/1988 | Kendall |
| 4,778,474 A | 10/1988 | Homsy |
| 4,792,337 A | 12/1988 | Müller |
| 4,795,469 A | 1/1989 | Oh |
| 4,795,470 A | 1/1989 | Goymann et al. |
| 4,798,610 A | 1/1989 | Averill et al. |
| 4,801,301 A | 1/1989 | Noiles |
| 4,808,186 A | 2/1989 | Smith |
| 4,813,960 A | 3/1989 | Muller |
| 4,822,367 A | 4/1989 | Stuhmer |
| 4,822,369 A | 4/1989 | Oneveau et al. |
| 4,834,759 A | 5/1989 | Spotorno et al. |
| 4,840,631 A | 6/1989 | Mathys |
| 4,840,632 A | 6/1989 | Kampner |
| 4,842,605 A | 6/1989 | Sonnerat et al. |
| 4,846,840 A | 7/1989 | Leclercq et al. |
| 4,865,609 A | 9/1989 | Roche |
| 4,878,916 A | 11/1989 | Rhenter et al. |
| 4,883,488 A | 11/1989 | Bloebaum et al. |
| 4,888,024 A | 12/1989 | Powlan |
| 4,891,551 A | 1/1990 | Will et al. |
| 4,892,549 A | 1/1990 | Figgie, III et al. |
| 4,904,265 A | 2/1990 | MacCollum et al. |
| 4,911,723 A | 3/1990 | Menschik |
| 4,919,676 A | 4/1990 | Zweymuller et al. |
| 4,921,500 A | 5/1990 | Averill et al. |
| 4,936,861 A | 6/1990 | Muller et al. |
| 4,955,325 A | 9/1990 | Zarnowski et al. |
| 4,960,427 A | 10/1990 | Noiles |
| 4,969,910 A | 11/1990 | Frey et al. |
| 4,978,356 A | 12/1990 | Noiles |
| 5,002,577 A | 3/1991 | Bolesky et al. |
| 5,004,476 A | 4/1991 | Cook |
| 5,009,665 A | 4/1991 | Serbousek et al. |
| 5,019,105 A | 5/1991 | Wiley |
| 5,021,062 A * | 6/1991 | Adrey et al. ............... 623/22.36 |
| 5,049,158 A | 9/1991 | Engelhardt et al. |
| 5,062,853 A | 11/1991 | Forte |
| 5,074,881 A | 12/1991 | Thull et al. |
| 5,080,674 A | 1/1992 | Jacobs et al. |
| 5,080,677 A | 1/1992 | Shelley |
| 5,080,678 A | 1/1992 | Spotorno et al. |
| 5,092,897 A | 3/1992 | Forte |
| 5,092,898 A | 3/1992 | Bekki et al. |
| 5,098,437 A | 3/1992 | Kashuba et al. |
| 5,108,445 A | 4/1992 | Ashby |
| 5,108,447 A | 4/1992 | Zeiler et al. |
| 5,108,449 A | 4/1992 | Gray |
| 5,108,452 A | 4/1992 | Fallin et al. |
| 5,133,764 A | 7/1992 | Pappas et al. |
| 5,156,625 A | 10/1992 | Marchetti et al. |
| 5,156,626 A | 10/1992 | Broderick et al. |
| 5,171,286 A | 12/1992 | Lawes et al. |
| 5,176,711 A | 1/1993 | Grimes |
| 5,217,499 A | 6/1993 | Shelley |
| 5,226,917 A | 7/1993 | Schryver |
| 5,263,986 A | 11/1993 | Noiles et al. |
| 5,263,988 A | 11/1993 | Huebner |
| 5,282,864 A | 2/1994 | Noiles et al. |
| 5,310,408 A | 5/1994 | Schryver et al. |
| 5,314,479 A | 5/1994 | Rockwood, Jr. et al. |
| 5,314,491 A | 5/1994 | Thongpreda et al. |
| 5,326,354 A | 7/1994 | Kwarateng |
| 5,326,368 A | 7/1994 | Collaza |
| 5,370,702 A | 12/1994 | Jones |
| 5,376,122 A | 12/1994 | Pappas et al. |
| 5,383,938 A | 1/1995 | Rohr et al. |
| 5,413,603 A | 5/1995 | Noiles et al. |
| 5,425,778 A | 6/1995 | Zichner et al. |
| 5,428,778 A | 6/1995 | Brookes |
| 5,443,519 A | 8/1995 | Averill et al. |
| 5,443,520 A | 8/1995 | Zweymüller et al. |
| 5,458,649 A | 10/1995 | Spotorno et al. |
| 5,480,448 A | 1/1996 | Mikhail |
| 5,486,181 A | 1/1996 | Cohen et al. |
| 5,507,824 A | 4/1996 | Lennox |
| 5,507,825 A | 4/1996 | Frei |
| 5,507,828 A | 4/1996 | Maumy et al. |
| 5,507,830 A | 4/1996 | DeMane et al. |
| 5,549,695 A | 8/1996 | Spotorno et al. |
| 5,549,696 A | 8/1996 | Willi |
| 5,549,698 A | 8/1996 | Averill et al. |
| 5,549,701 A | 8/1996 | Mikhail |
| 5,571,201 A | 11/1996 | Averill et al. |
| 5,624,464 A | 4/1997 | Wagner et al. |
| 5,645,594 A | 7/1997 | Devanathan et al. |
| 5,658,338 A | 8/1997 | Tullos et al. |
| 5,658,345 A | 8/1997 | Willi |
| 5,676,704 A | 10/1997 | Ries et al. |
| 5,702,478 A | 12/1997 | Tornier |
| 5,725,587 A | 3/1998 | Garber |
| 5,725,589 A | 3/1998 | Pfaff et al. |
| 5,725,591 A | 3/1998 | DeCarlo, Jr. et al. |
| 5,755,808 A | 5/1998 | DeCarlo et al. |
| 5,766,260 A | 6/1998 | Whiteside |
| 5,782,928 A | 7/1998 | Ries et al. |
| 5,782,929 A | 7/1998 | Sederholm |
| 5,800,555 A | 9/1998 | Gray, III |
| 5,800,556 A | 9/1998 | Sanders et al. |
| 5,824,107 A | 10/1998 | Tschirren |
| 5,824,108 A | 10/1998 | Huebner |
| 5,879,397 A | 3/1999 | Kälberer et al. |
| 5,879,401 A | 3/1999 | Besemer et al. |
| 5,879,404 A | 3/1999 | Bateman et al. |
| 5,879,405 A | 3/1999 | Ries et al. |
| 5,919,236 A | 7/1999 | Pfaff et al. |
| 5,935,175 A | 8/1999 | Ostiguy, Jr. et al. |
| 5,938,702 A | 8/1999 | Lopez et al. |
| 5,997,579 A | 12/1999 | Albrektsson et al. |
| 6,027,505 A | 2/2000 | Peter et al. |
| 6,045,583 A | 4/2000 | Gross et al. |
| 6,059,833 A | 5/2000 | Doets |
| 6,132,469 A | 10/2000 | Schroeder |
| 6,152,961 A | 11/2000 | Ostiguy, Jr. et al. |
| 6,162,256 A | 12/2000 | Ostiguy, Jr. et al. |
| 6,162,257 A | 12/2000 | Gustilo et al. |
| 6,358,282 B1 | 3/2002 | Wymann |
| 6,368,354 B2 | 4/2002 | Burstein et al. |
| 6,379,389 B1 | 4/2002 | Koch |
| 6,537,321 B1 | 3/2003 | Horber |

(56) References Cited

U.S. PATENT DOCUMENTS

| | | | |
|---|---|---|---|
| 6,589,284 | B1 | 7/2003 | Silberer |
| 6,610,097 | B2 | 8/2003 | Serbousek et al. |
| 2003/0212459 | A1* | 11/2003 | Gibbs .................... 623/22.32 |

FOREIGN PATENT DOCUMENTS

| | | |
|---|---|---|
| CH | 669904 A5 | 4/1989 |
| DE | 2950536 A1 | 7/1981 |
| DE | 3215583 A1 | 12/1982 |
| DE | 8500869 U1 | 12/1985 |
| DE | 3602081 A1 | 10/1986 |
| DE | 19620750 C1 | 1/1990 |
| DE | 0456580 A1 | 11/1991 |
| DE | 9110508 U1 | 12/1991 |
| DE | 4142920 A1 | 7/1993 |
| DE | 4222218 A1 | 1/1994 |
| DE | 4304022 A1 | 8/1994 |
| DE | 9402847.8 U1 | 9/1994 |
| DE | 4325701 A1 | 2/1995 |
| DE | 9418900 U1 | 3/1995 |
| DE | 4335931 A1 | 4/1995 |
| DE | 29517637 U1 | 1/1996 |
| DE | 4435698 A1 | 4/1996 |
| DE | 19616058 A1 | 10/1997 |
| DE | 19620750 C1 | 1/1998 |
| DE | 19640747 A1 | 2/1998 |
| DE | 19701536 A1 | 2/1998 |
| DE | 19654409 C1 | 4/1998 |
| DE | 19701778 A1 | 6/1998 |
| DE | 69407667 T2 | 8/1998 |
| DE | 69411770 T2 | 1/1999 |
| DE | 19746997 A1 | 4/1999 |
| DE | 29907342 U1 | 9/1999 |
| EP | 0041019 A2 | 12/1981 |
| EP | 0065482 A2 | 12/1982 |
| EP | 0066092 A1 | 12/1982 |
| EP | 0091315 A1 | 10/1983 |
| EP | 091315 A1 | 10/1983 |
| EP | 0123514 A1 | 10/1984 |
| EP | 150198 A1 | 1/1985 |
| EP | 0142759 A2 | 5/1985 |
| EP | 0190093 A1 | 8/1985 |
| EP | 0190093 A1 | 8/1986 |
| EP | 0242633 B1 | 10/1987 |
| EP | 0245527 A1 | 11/1987 |
| EP | 0277511 A1 | 8/1988 |
| EP | 0297789 A1 | 1/1989 |
| EP | 0298234 A1 | 1/1989 |
| EP | 0313762 A1 | 5/1989 |
| EP | 0313762 B1 | 5/1989 |
| EP | 0313773 A1 | 5/1989 |
| EP | 0318679 B1 | 6/1989 |
| EP | 0339530 A2 | 11/1989 |
| EP | 0357302 A1 | 3/1990 |
| EP | 0234811 B1 | 4/1990 |
| EP | 0394545 B1 | 10/1990 |
| EP | 0407332 A1 | 1/1991 |
| EP | 0420795 B1 | 4/1991 |
| EP | 0433121 B1 | 6/1991 |
| EP | 0296274 B1 | 7/1991 |
| EP | 0436317 A1 | 7/1991 |
| EP | 0291562 B1 | 9/1991 |
| EP | 0444381 B1 | 9/1991 |
| EP | 0444382 B1 | 9/1991 |
| EP | 0445068 A1 | 9/1991 |
| EP | 0453694 A1 | 10/1991 |
| EP | 0457222 B1 | 11/1991 |
| EP | 0485326 B1 | 5/1992 |
| EP | 0485678 A1 | 5/1992 |
| EP | 0488943 B1 | 6/1992 |
| EP | 0501207 B1 | 9/1992 |
| EP | 0532439 A2 | 3/1993 |
| EP | 0404680 B1 | 5/1993 |
| EP | 0554214 A1 | 8/1993 |
| EP | 0563503 B1 | 10/1993 |
| EP | 0567349 A1 | 10/1993 |
| EP | 0585503 B1 | 3/1994 |
| EP | 0601224 B1 | 6/1994 |
| EP | 0629386 A2 | 12/1994 |
| EP | 0636351 A2 | 2/1995 |
| EP | 0638299 A1 | 2/1995 |
| EP | 0694294 A1 | 1/1996 |
| EP | 0722703 A2 | 7/1996 |
| EP | 0728499 A2 | 8/1996 |
| EP | 07282448 A1 | 8/1996 |
| EP | 0638299 B1 | 5/1997 |
| EP | 0773007 A1 | 5/1997 |
| EP | 0807426 A2 | 11/1997 |
| EP | 0815809 A2 | 1/1998 |
| EP | 0867158 A2 | 9/1998 |
| EP | 0888759 A1 | 1/1999 |
| EP | 0901777 A2 | 3/1999 |
| EP | 0927547 A2 | 7/1999 |
| EP | 0945109 A2 | 9/1999 |
| EP | 0958797 A1 | 11/1999 |
| EP | 0682507 B1 | 6/2000 |
| EP | 0732903 B1 | 9/2000 |
| EP | 0748193 B1 | 12/2001 |
| EP | 0793461 B1 | 6/2003 |
| EP | 0695153 B1 | 4/2004 |
| ES | 263394 U | 4/1984 |
| ES | 263394 | 5/1984 |
| ES | 263394 U | 5/1984 |
| FR | 2301217 A2 | 9/1976 |
| FR | 2377798 A2 | 8/1978 |
| FR | 2417972 A1 | 9/1979 |
| FR | 2597329 A1 | 10/1987 |
| FR | 2628314 A1 | 9/1989 |
| FR | 2628967 A1 | 9/1989 |
| FR | 2641461 A1 | 7/1990 |
| FR | 2653326 A2 | 4/1991 |
| FR | 2682588 A1 | 4/1993 |
| FR | 2686790 A1 | 8/1993 |
| FR | 2700946 A1 | 8/1994 |
| FR | 2765100 A1 | 12/1998 |
| GB | 1334584 | 10/1973 |
| GB | 1521880 | 8/1978 |
| GB | 2116847 A | 10/1983 |
| GB | 2126096 A | 3/1984 |
| GB | 2159416 A | 12/1985 |
| GB | 2203948 A | 11/1988 |
| IT | 01292412 | 2/1999 |
| IT | 01292412 | 8/1999 |
| JP | 62254748 A | 11/1987 |
| JP | 62254748 A2 | 11/1987 |
| JP | 1158950 A2 | 6/1989 |
| JP | 4044756 A2 | 2/1992 |
| JP | 5137738 A2 | 6/1993 |
| JP | 5208027 A2 | 8/1993 |
| JP | 5344991 A2 | 12/1993 |
| JP | 5344992 A | 12/1993 |
| JP | 5344992 A2 | 12/1993 |
| JP | 6285098 F1 | 10/1994 |
| JP | 800651 A | 1/1996 |
| JP | 8294501 A2 | 11/1996 |
| JP | 9038120 A2 | 2/1997 |
| JP | 10-14957 A2 | 1/1998 |
| JP | 1014957 A | 1/1998 |
| RU | 980709 | 12/1982 |
| RU | 2021786 C1 | 10/1994 |
| RU | 2071299 C1 | 1/1997 |
| RU | 2092132 C1 | 10/1997 |
| RU | 2108071 C1 | 4/1998 |
| SU | 1680149 A1 | 9/1991 |
| SU | 1711867 A1 | 2/1992 |
| WO | 86/02261 A1 | 4/1986 |
| WO | 91/07932 A1 | 6/1991 |
| WO | 91/16015 A1 | 10/1991 |
| WO | 92/15261 A1 | 9/1992 |
| WO | 93/03687 A1 | 3/1993 |
| WO | 94/21199 A1 | 9/1994 |
| WO | 94/23670 A1 | 10/1994 |
| WO | 95/22944 A1 | 8/1995 |

(56) References Cited

FOREIGN PATENT DOCUMENTS

| WO | 95/25483 A1 | 9/1995 |
|---|---|---|
| WO | 96/13231 A1 | 5/1996 |
| WO | 9716137 A1 | 5/1997 |
| WO | 97/19656 A1 | 6/1997 |
| WO | 99/43274 A1 | 2/1999 |
| WO | 99/22672 A2 | 5/1999 |
| WO | 99/22674 A1 | 5/1999 |
| WO | 99/43274 A1 | 9/1999 |

OTHER PUBLICATIONS

Star, et al., "Dissociation of Modular Hip Arthroplasty Components After Dislocation", Division of Orthopaedic Surgery, Scripps Clinic and Research Foundation, La Jolla, CA, May 1992.

Collier, et al., "Corrosion Between the Components of Modular Femoral Hip Prostheses", J Bone Joint Surg [Br] 1992; 74-B; 511-7.

Gilbert, et al., "In Vivo corrosion of modular hip prosthesis components in mixed and similar metal combinations. The effect of crevice, stress, motion, and alloy coupling", Journal of Biomedical Materials Research, vol. 27, 1553-1544 (1993).

Witvoët, et al., "Total hip arthroplasty with a titanium threaded acetabular ring. Outcome of 446 prostheses with an average follow-up time of 4 years", The Journal of Orthopaedic Surgery, 1993, 7, No. 4, 429-438.

Bobyn, et al., "Concerns with Modularity in Total Hip Arthroplasty, Clnical Orthopaedics and Related Research", No. 298, pp. 27-36, 1994.

Cook, et al., "Wear and Corrosion of Modular Interfaces in Total Hip Replacements", Clinical Orthopaedics and Related Research, No. 298, pp. 80-88, 1994.

Whiteside, 35 al., "Fixation of the Modular Total Hip Femoral Component in Cementless Total Hip Arthroplasty", Clinical Orthopaedics and Related Research, No. 298, pp. 184-190, 1994.

Chmell, et al., "The Implact of Modularity in Total Hip Arthroplasty", Clinical Orthopaedics and Related Research, No. 319, pp. 77-84, 1995.

Jacobs, et al., "Local and distant Products from Modularity", Clinical Orthopaedics and Related Research, No. 319, pp. 94-105, 1995.

Collier, et al., "The Tradeoffs Associated With Modular Hip Prostheses", Clinical Orthopaedics and Related Research, No. 311, pp. 91-101, 1995.

Salvati, et al., "Complications of Femoral and Acetabular Modularity", Clinical Orthopaedics and Related Research, No. 319, pp. 85-93, 1995.

Cameron, "Modularity in Primary Total Hip Arthroplasty", The Journal of Arthroplasty, vol. 11, No. 3, 1996.

Harris, Modularity is Unnecessary in Primary Femoral THA But Has Some Advantages in Primary Acetabular THA, The Journal of Arthroplasty, vol. 11, No. 3, Apr. 1996.

McCarthy, et al., "Custom and Modular Components in Primary Total Hip Replacement", Clinical Orthopaedics and Related Research, No. 344, pp. 162-171, 1997.

Christie, et al., "Primary Total Hip Arthroplasty with Use of the Modular S-RO"M Prosthesis", The Journal of Bone and Joint Surgery, Incorporated, vol. 81-A., No. 12, Dec. 1999.

Baleani, et al., "Initial Stability of a Cementless Acetabular Cup Design: Experimental Investigation on the Effect of Adding Fins to the Rim of the Cup", Artificial Organs, 25(8) 664-669, Blackwell Science, Inc. 2001.

Epinette, et al., "A 10-Year Minimum Follow-Up of Hydroxyapatite-Coated Threaded Cups", The Journal of Arthroplasty, vol. 18, No. 2, 2003.

Neumann, et al., "Long-Term Results of a Contemporary Metal-on-Metal Total Hip Arthroplasty", The Journal of Arthroplasty, vol. 25, No. 5, 2010.

Capello, et al., "Alternative Bearing Surfaces: Alumina Ceramic Bearings for Total Hip Arthroplasty", Clinical Results of Ceramic on Ceramic Systems.

Garino, "1.8 Design Considerations and Preliminary Results with the Wright Medical,,Transcend" Acetabular Cup System, Proceedings of the 3rd International Symposium on Ceramic Wear Couple, Feb. 14, 1998 Stuttgart (Germany).

Swanson, et al., Poster—"Influence of Prosthetic Design on Squeaking After Ceramic-on-Ceramic Total Hip Arthroplasty".

Willert, "Clinical Relevance of Wear Particles to Osteolysis and Loosening of Hip Endoprostheses", Proceedings des. 1 Cerasiv-Symposiums am Mar. 23, 1996 in Stuttgart.

Willert, "Our Experiences with Ceramic on Polyethylene Bearing in Total Hip Arthroplasties", Die Keramikpaarung Biolox in der Hüftendoprothetik, Proceedings des. 1. Cerasiv-Symposiums am Mar. 23, 1996 in Stuttgart.

Fritsch, et al., "Biocompatibility of Alumina-Ceramic in Total Hip Replacement. Macroscopic- and Microscopic Findings on Capsular Tissues after Long-term Implantation", Die Keramikpaarung Biolox in der Hüftendoprothetik, Proceedings des 1. Cerasiv-Symposiums am Mar. 23, 1996 in Stuttgart.

Bos, et al., "Morphologic Characteristics of Joint Capsules around Hip Prostheses with Alumina on Alumina Combinations. Histologic Investigations of Revision- and Autopsy Cases", Die Keramikpaarung Biolox in der Hüftendoprothetik, Proceedings des 1. Cerasiv-Symposiums am Mar. 23, 1996 in Stuttgart.

Stock, Long-term Experience with Al2O3 Ceramic-on-Ceramic Combinations at the Hip since 1974, The Ceramic Combination Biolox in Hip Endoprosthetics, Proceedings of the Cerasiv Symposium on Mar. 23, 1996, in Stuttgart.

Sedel, "Long-term Clinical Results of All Alumina Bearings", Die Deramikpaarung Biolox in der Hüftendoprothetik, Proceedings des 1. Cerasiv-Symposiums am Mar. 23, 1996 in Stuttgart.

Parrini, et al., "3.5 Survivorship Analysis and Results of Acetabular Component in Primary Alumina-Alumina Hip Replacement", Die Deramikpaarung Biolox in der Hüftendoprothetik, Proceedings des 1. Cerasiv-Symposiums am Mar. 23, 1996 in Stuttgart.

Ravasi, "Preliminary Report on a New Coupling System for Alumina-Alumina Total Hip Replacement", Die Deramikpaarung Biolox in der Hüftendoprothetik, Proceedings des 1. Cerasiv-Symposiums am Mar. 23, 1996 in Stuttgart.

Rueda, "Long-term Response (10-15 years) to Threaded Ceramic Acetabular Cups", Die Deramikpaarung Biolox in der Hüftendoprothetik, Proceedings des 1. Cerasiv-Symposiums am Mar. 23, 1996 in Stuttgart.

Lubinus, "3.8 The Necessity of Preoperative Planning Using the Ceramic Wear Couple", Die Deramikpaarung Biolox in der Hüftendoprothetik, Proceedings des 1. Cerasiv-Symposiums am Mar. 23, 1996 in Stuttgart.

Guerzoni, et al., "3.10 Cotyloid Bone Resorption with Endopelvic Migration of the Acetabular Cupola in Total Hip Bioceramic Prostheses", Die Deramikpaarung Biolox in der Hüftendoprothetik, Proceedings des 1. Cerasiv-Symposiums am Mar. 23, 1996 in Stuttgart.

Richter, et al., "4.3 Reliability of Ceramic Components for Total Hip Endoprostheses", Die Deramikpaarung Biolox in der Hüftendoprothetik, Proceedings des 1. Cerasiv-Symposiums am Mar. 23, 1996 in Stuttgart.

Pria, "4.4 Recent Innovations Relating to the Use of Ceramic-Ceramic Hip Joint Prostheses", Die Deramikpaarung Biolox in der Hüftendoprothetik, Proceedings des 1. Cerasiv-Symposiums am Mar. 23, 1996 in Stuttgart.

Furlong, "The Future for Prosthetic Fixation—Histology of a 9 Year Osprovit Explant", Die Deramikpaarung Biolox in der Hüftendoprothetik, Proceedings des 1. Cerasiv-Symposiums am Mar. 23, 1996 in Stuttgart.

Willmann, "Modularity—The Chance to Solve the Wear Problems in Total Hip Replacement", Die Deramikpaarung Biolox in der Hüftendoprothetik, Proceedings des 1. Cerasiv-Symposiums am Mar. 23, 1996 in Stuttgart.

Black, "1.1 Prospects for Alternate Bearing Surfaces in Total Replacement Arthroplasty of the Hip", Performance of the Wear Couple Biolox forte in HIP Arthroplasty, Proceedings of the 2nd Symposium on Ceramic Wear Couple Mar. 8, 1997 Stuttgart (Germany).

Jerosch, et al., "1.2 Probleme des Implantatwerkstoffes ultrahochmolekulares Polyethylen (UHMWPE)", Performance of

(56) References Cited

OTHER PUBLICATIONS the Wear Couple Biolox forte in HIP Arthroplasty, Proceedings of the 2nd Symposium on Ceramic Wear Couple Mar. 8, 1997 Stuttgart (Germany).
Toni, et al., "2.1 Ceramic in Total Hip Arthroplasty", Performance of the Wear Couple Biolox forte in Hip Arthroplasty, Proceedings of the 2nd Symposium on Ceramic Wear Couple Mar. 8, 1997 Stuttgart (Germany).
Fantasia, et al., "2.2 A Bipolar Cup with Ceramic Insert for the Hip Degenerative Pathology: Early Experiences", Performance of the Wear Couple Biolox forte in Hip Arthroplasty, Proceedings of the 2nd Symposium on Ceramic Wear Couple Mar. 8, 1997 Stuttgart (Germany).
Bonicoli, et al., "2.3 Ceramic Insert in Uncemented Press-fit Titanium Total Hip Prostheses. Our Clinical Experience in Fifty-nine Cases", Performance of the Wear Couple Biolox forte in Hip Arthroplasty, Proceedings of the 2nd Symposium on Ceramic Wear Couple Mar. 8, 1997 Stuttgart (Germany).
Rueda, et al., 2.4 Ceramic Inserts in Metal Cups. A Five-year Experience, Performance of the Wear Couple Biolox forte in Hip Arthroplasty, Proceedings of the 2nd Symposium on Ceramic Wear Couple Mar. 8, 1997 Stuttgart (Germany).
Fenollosa, et al., "2.5 Ceramic-ceramic in THR. Fifteen years of experience, with 262 cases", Performance of the Wear Couple Biolox forte in Hip Arthroplasty, Proceedings of the 2nd Symposium on Ceramic Wear Couple Mar. 8, 1997 Stuttgart (Germany).
Gualtieri, et al., "2.6 Hip Arthroprosthesis with Ceramic to Ceramic Coupling: Experimental Tests and Clinical Trials", Performance of the Wear Couple Biolox forte in Hip Arthroplasty, Proceedings of the 2nd Symposium on Ceramic Wear Couple Mar. 8, 1997 Stuttgart (Germany).
Franke, et al., "2.8 Monolithische versus modular aufgebaute, zementfreie Keramik-Hüft-Endoprothesen", Performance of the Wear Couple Biolox forte in Hip Arthroplasty, Proceedings of the 2nd Symposium on Ceramic Wear Couple Mar. 8, 1997 Stuttgart (Germany).
Franke, et al., "2.8 English Version—Monolithic versus modularly designed, cement-less ceramic hip endoprostheses".
Stock, 3.3 Die Langzeiterfahrung mit A1s03-Keramikgleitpaarungen an der Hüfte seit 1974, The Ceramic Combination Biolox in Hip Endoprosthetics, Proceedings of the Cerasiv Symposium on Mar. 23, 1996, in Stuttgart.
Garino, "3.1 The United States Food and Drug Administration and its Regulation of Medical Devices", Performance of the Wear Couple Biolox forte in Hip Arthroplasty. Proceedings of the 2nd Symposium on Ceramic Wear Couple Mar. 8, 19979 Stuttgart (Germany).
Bombelli, et al. "Abstracts from II Meeting of the Italian Hip Society (COXA)", Bologna, IT, Nov. 28, 1997 (Hip International 1998; 8: 31-37).
Baleani, et al., "Metallic wear debris in dual modular hip arthroplasty", Capelli editore, Bologna 1997, Chir. Organi Mou., LXXXII, 231-238, 1997.
Bohler, 3.2 Results of metal-backed cup prostheses with ceramic inlay and a follow-up time of >4 years, Implantation 1990, 12, Fig. 3.2.5a, b.
Blömer, "3.2 Design Aspects of Modular Inlay Fixation", Performance of the Wear Couple Biolox forte in Hip Arthroplasty, Proceedings of the 2nd Symposium on Ceramic Wear Couple Mar. 8, 1997 Stuttgart (Germany).
Willmann, "Biolox® forte Heads and Cup Inserts for THR—What a Surgeon Should Know", Performance of the Wear Couple Biolox forte in Hip Arthroplasty, Proceedings of the 2nd Symposium on Ceramic Wear Couple Mar. 8, 1997 Stuttgart (Germany).
Saikko, et al., "3.4 Wear of Alumina-on-alumina Total Replacement Hip Joints Studied with a Hip Joint Simulator", Performance of the Wear Couple Biolox forte in Hip Arthroplasty, Proceedings of the 2nd Symposium on Ceramic Wear Couple Mar. 8, 1997 Stuttgart (Germany).
Walter, "3.5 Investigations on the Wear Couple Biolox® forte/ Biolox® forte and Earlier Alumina Materials", Performance of the Wear Couple Biolox forte in Hip Arthroplasty, Proceedings of the 2nd Symposium on Ceramic Wear Couple Mar. 8, 1997 Stuttgart (Germany).
Pria, et al., "3.6 Stiffness of the Acetabular Cups: A Comparative Study Using the Finite Element Method", Performance of the Wear Couple Biolox forte in Hip Arthroplasty, Proceedings of the 2nd Symposium on Ceramic Wear Couple Mar. 8, 1997 Stuttgart (Germany).
Siverhus, "1.1 Design Considerations and Preliminary Results with the Osteonics Acetabular Cup System", Bioceramics in Orthopaedics—New Applications, Proceedings of the 3rd International Symposium on Ceramic Wear Couple, Feb. 14, 1998 Stuttgart (Germany).
Richter, "Application of Proof-Testing to Ceramic Hip Joint Heads", Bioceramics in Orthopaedics—New Applications, Proceedings of the 3rd International Symposium on Ceramic Wear Couple, Feb. 14, 1998 Stuttgart (Germany).
Willmann, et al., "1.3 Investigation of 87 Retrieved Ceramic Femoral Heads", Bioceramics in Orthopaedics—New Applications, Proceedings of the 3rd International Symposium on Ceramic Wear Couple, Feb. 14, 1998 Stuttgart (Germany).
Cremascoli Ortho Group, "ANCA-Fit Brochure".
Cremascoli Ortho Group, "ANCA-Fit Surgical Technique".
LIMA-LTO, "SPH Cup System uncemented", The Journal of Bone and Joint Surgery—53.
Böhler, et al., "Ergebnisse mit der Keramik-Keramik-Gleitpaarung in der Hüftendoprothetik", Die Keramikpaarung Biolox in der Hüftendoprothetik, Proceedings des. 1. Cerasic-Symposiums am Mar. 23, 1996 in Stuttgart.
Toni, et al., "2.1 Ceramic in Total Hip Arthroplasty", Performance of the Wear Couple Biolox forte in Hip Arthroplasty Proceedings of the 2nd Symposium on Ceramic wear Couple, Mar. 8, 1997 Stuttgart (Germany).
Toni, et al., Anatomic cementless total hip arthroplasty with ceramic bearings and modular necks: 3 to 5 years follow-up, Hip International / vol. 11 No. 1, 2001, pp. 1-17.
Zweymüller, "Alloclassic® Cups CSF Cementless" Product Information.
Zimmer, "The Alloclassic® Zweymüller® CSF Screw Cup" Product Information.
Karamat, et al., "3.6 Blood analysis for Trace Metals in Metal-on-Metal and Ceramic-on-Ceramic Bearings in Total Hip Arthroplasty", 7th Biolox Symposium.
Allopro, "Cups Armor Cementless—Product Information", Sulzer Orthopedics Ltd. 1997, Lit. No. 2010 e Ed. Nov. 1995 p.
Randelli, et al., "Cementless Metasul Metal-on-Metal Total Hip Arthroplasties at 13 Years", The Journal of Arthroplasty vol. 27, No. 2 2012.
Willmann, et al., "1.4 The Improvements of the Material Properties of Biolox Offer Benefits for THR", Bioceramics in Orthopaedics—New Applications, Proceedings of the 3rd International Symposium on Ceramic Wear Couple, Feb. 14, 1998 Stuttgart (Germany).
Kaddick, et al., "Determination of Resistance to Luxations/Repositions of Total Hip Joint Prostheses", Bioceramics in Orthopaedics—New Applications, Proceedings of the 3rd International Symposium on Ceramic Wear Couple, Feb. 14, 1998 Stuttgart (Germany).
Pfaff, et al., "1.6 Stability of Y-TZP Zirconia", Bioceramics in Orthopaedics—New Applications, Proceedings of the 3rd International Symposium on Ceramic Wear Couple, Feb. 14, 1998 Stuttgart (Germany).
Garino, "Design Considerations and Preliminary Results with the Wright Medical,,Transcent Acetabular Cup System", Bioceramics in Orthopaedics—New Applications, Proceedings of the 3rd International Symposium on Ceramic Wear Couple, Feb. 14, 1998 Stuttgart (Germany).
Inaraja, et al., "Radiological Analysis of the Interface Tissue-HA", Bioceramics in Orthopaedics—New Applications, Proceedings of the 3rd International Symposium on Ceramic Wear Couple, Feb. 14, 1998 Stuttgart (Germany).
Degreif, et al., "3.1 Clinical Experience with Biolox® forte in Hemiarthroplasty", Bioceramics in Orthopaedics—New Applications, Proceedings of the 3rd International Symposium on Ceramic Wear Couple, Feb. 14, 1998 Stuttgart (Germany).

(56) References Cited

OTHER PUBLICATIONS

Conta, et al., "4.1 Polyethylene—The Weak Link in Total Knee Replacement", Bioceramics in Orthopaedics—New Applications, Proceedings of the 3rd International Symposium on Ceramic Wear Couple, Feb. 14, 1998 Stuttgart (Germany).
Badorf, "4.2 Ceramics in Total Knee Replacement—A New Concept", Bioceramics in Orthopaedics—New Applications, Proceedings of the 3rd International Symposium on Ceramic Wear Couple, Feb. 14, 1998 Stuttgart (Germany).
Garino, "4.3 State of the Art of Total Knee Arthroplasty in the United States", Bioceramics in Orthopaedics—New Applications, Proceedings of the 3rd International Symposium on Ceramic Wear Couple, Feb. 14, 1998 Stuttgart (Germany).
Willmann, "61. A Bibliography of Published Literature on Bioceramics for THR", Bioceramics in Orthopaedics—New Applications, Proceedings of the 3rd International Symposium on Ceramic Wear Couple, Feb. 14, 1998 Stuttgart (Germany).
Wright Medical Technology, "Alumina on alumina bearing surfaces transcend existing metal on poly systems", Transcend Articulation System, 1996.
Bläsius, et al., "Hüftpfannen: Verankerungstechniken und Pfannenwanderung", Springer/Implant 95-96.
Osteonics, "Osteonics™ Secur-Fit™ HA Ceramic on Ceramic Bearing System".
Wright Medical Technology, "Metal on metal articulation", Transcend Articulation System, 1997.
Willmann, et al, "1.9 2-4 Year Clinical Results with a Ceramic-on-Ceramic Articulation in a New Modular THR-System, Bioceramics in Hip Joint Replacement", Proceedings 5th International CeramTec Symposium, Feb. 18/19, 2000, pp. 39-45.
Quack, "Design Consideratiaon to Improve the Acetabular Cup of the ESKA-THR System by Using the Wear Couple Ceramic-on-Ceramic", Biomedical Engineering, vol. 41, Issue Sep. 1996.
Quack, "Konzeptionelle Überlegungen zur Verbesserung der Pfanne der ESKA-Hüftendoprothese durch die Gleitpaarung Keramik-Keramik", Biomedizinische Technik, vol. 41, 1996, 253-259.
Wilkinson, et al., "Experiences with the Plastmacup—early stability, wear, remodelling, and outcome", Interntional Orthopaedics (SICOT) 2003, 27 (Suppl.1):S16-S19.
Dohmae, "Plasmacup—special design. Aspects of the dysplastic acetabulum", International Orthopaedics (SICOT) (2003) 27 (Suppl. 1): S20-S23.
Ochs, et al., "EBRA Migration Patterns of the Plasmacup with Ceramic or Polyethylene Inserts: A Randomised Study", Z Orthop Unfall 2007; 145: S20-S24.
Aesculap Product Overview.
Willmann, "4.6 Modularity—The Chance to Solve the Wear Problems in Total Hip Replacement".
"Acetabular Cups", Orthopaedic Product News May/Jun. 1997.
Rueda, et al., "2.4 Ceramic Inserts in Metal Cups. A Five-year Experience", Performance of the Wear Couple Biolox forte in Hip Arthroplasty, Proceedings of the 2nd Symposium on Ceramic Wear Couple, Mar. 8, 1997 Stuttgart (Germany).
Delaunay, et al., "Cementless primary total hip replacement", International Orthopaedics (SICOT) 1998, 22: 1-5.
Pieringer, et al., "Long-term Results of the Cementless Alloclassic Hip Arthroplasty System Using a 28-mm Ceramic Head", The Journal of Arthroplasty, vol. 21, No. 7 2006.
Fuchs, "2.4 Year Clnical Results with a Ceramic-on-Ceramic Articulation in a New Modular THR System", 5th Biolox Symposium, 2000—English Translation.
Sharma, et al., Metal-on_Metal Total Hip Joint Replacement: (A Minimum of 5-Year Follow-Up), J Bone Joint Surg Br 2008 vol. 90-0B, No. Supp II 299-300.
Smith & Nephew Richards, Axis™ Hip System Nov. 1996.
Intraplant AG, "Lubrimet® The Solid Metal/Metal Articulation".
Intraplant AG, Lubricer® The Stable Ceramic/Ceramic Articulation.
Metzner, et al., "Long-Term Results of the Cementless Hofer-Imhof Threaded Titanium Cup", Z Orthop Unfall 2009; 147: 166-174.
Neumann, et al., "Long-Term Results of a Contemporary Metal-on-Metal Total Hip Arthroplasty", The Journal of Arthroplasty vol. 25, No. 5 2010.
Neumann, et al., "Long Term Results of the Hofer-Imhof® Self-Reaming, Threaded Cup", 8th EFORT Congress—Florence May 11-15, 2007.
Neumann, et al., "Mid-Term Results of the Hofer-Imhof Lubrimet® Metal-on-Metal Articulation" Presentation.
Neumann, et al., Mid-Term Results of the Hofer-Imhof Lubrimet® Metal-on-Metal Articulation, Poster.
Dorn, et al., "The Metal-on-Metal Sliding Combination Concerning for the HI Socket", Compendium of the Symposium on Apr. 25, 1998 in Salzburg, Prim. Univ. Doz. Dr. Ulrich Dorn.
Intraplant, Surgery Technique H-I threaded cup (int.pat), according to Prof. H. Hofer, Salzburg.
Dr. Med, et al., "EPF—Acetabular Cup", Plus Endoprothetik, Apr. 1997.
Böhler, et al., "Influence of Different Layers on Migration of Cementless Press-Fit Sockets", JBJS 1997.
Rieger, "Ceramics in Orthopedics—30 Years of Evolution and Experience", Hans Huber 2001.
Swanson, "Ceramic-on-Ceramic THA: The Good with the Bad", Jan. 1908.
Oberg, et al., "Machinery's Handbook", 24th Edition, Industrial Press Inc. 1992.
"The S-ROM™ Total Hip System—Addresses the Issues", Joint Medical Product Corporation, 1993.
"The S-ROM® ZTT™ Acetabular Cup, a Step Ahead", Joint Medical Product Corporation 1994.
Intraplant, "Product Information Modular Press Fit Cup MPF Surgical Technique", Jun. 1999.
Menge, et al., "Mittelfristige Ergebnisse mit dem SI-Schraubring mit Keramik-Inserts", Mar. 8, 1997.
Garino, "Design Considerations and Preliminary Results with the Wright Medical "Transcend" acetabular Cup System", Feb. 14, 1998.
"Transcend Articulation System, Alumina on alumina bearing surfaces", Wright Medical Technology, 1996.
"Contact SPH Cups System non-cemented", XLima-Lto Medical Systems.
Fuchs, "2-4 Year Clinical Results with a Ceramic-on-Ceramic Articulation in a New Modular THR-System", Bioceramics in Hip Joint Replacement Proceedings 5th International CeramTec Symposium, Feb. 18/19, 2000, Edited by Willmann and Zweymüller.
"ESKA-Implants Hüft-Endoprothesensystem" Product Flyer, ESKA-Implants, Feb. 1997.
Blömer, "Design Aspects of Modular Inlay Fixation", Mar. 8, 1997.
"Acetabular Cups", Orthopaedic Product News, May 6, 1997.
Franke, et al., "Monolithische versus modular aufgebaute, zementfreie Keramik-Hüft-Endoprothesen", 1997.
"1970-1995 Our Osteolysis Challenge: A Successful Story with 25 Years Experience", Ceraver Osteal, May 1995.
Bonicoli, et al., "Ceramic Insert in Uncemented Press-fit Titanium Total Hip Prostheses. Our Clinical Experience in Fifty-nine Cases", Performance of the Wear Couple Biolox forte in Hip Arthroplasty, Proceedings of the 2nd Symposium on Ceramic Wear Couple, Mar. 8, 1997 Stuttgart (Germany).
Willmann, et al., "Keramische Pfanneneinsätze für Hüftendoprothesen, Ceramic Cup Inserts for Hip Endoprostheses,", Biomed. Technik 41 (1996, 98-105).
Bädorf, et al., "Klinische Fakten zur Gleitpaarung Keramik/Keramik", Cerasiv Product Information.
"The Origihnal Furlong® Hydroxyapatite Ceramic (Osprovit)® Coated Total Hip Replacement", Joint Replacement Instrumentation Ltd, 1988.
Witvoët, "Arthroplastie totale de hanche avec anneau cotyloïdien en titane Vissé Devenir de 446 prothèses avec un recul moyen de 4 ans, Total hip arthroplasty with a titanium threaded cup. Survivorhip analysis of 508 cups", Revue de Chirurgie Orthopèdique 1993, 79, 542-552.
Howmedica P.C.A.® total hip system, Howmedica.
Zweymüller, "Alloclassic® Cups CSF Cementless Product Information", Allopro AG, 1993.

(56) References Cited

OTHER PUBLICATIONS

Willert, Zementiertes CF Hüft-Endoprothesensystem Mit Zentrierhilfe Produktinformation, Allopro AG, 1992.
Han, et al., "Late Dissociation of the Polyethylene Liner from a Modular Acetabular Metal Shell after Primary Total Hip Arthroplasty", Yonsei Medical Journal, vol. 39, No. 3, pp. 227-282, 1998.
"ABG II Acetabular Cup System", Advertisement, Journal of Bone and Joint Surgery, vol. 78-B, 1996.
Delaunay, et al., "Acetabular screw rings and surface treatments. A series of 115 consecutive primary acetabular arthroplasties with the Karl Zwelmüller threaded cup with a 5.8 years average follow-up", Revue de Chirurgie Orthopèdique 1994, 80, 338-402.
Bläsius, et al., "CLS-Multicenter-Studie—8jährige Erfahrungen", Z. Orthop. 131 (1993) 547-552.
Effenberger, "Radiological Results of the Hofer-Imhof (HI) Threaded Cup", W. Zuckschwerdt Verlag, 1996.
"Alloclassic® Stems SL Cementless" Product Information, Allopro AG, Switzerland 1993.
Schmidt, "The Alloclassic Hip System", Sulzermedica, Switzerland, medicaljournal 1995, 14-17.
Zweymüller, "Alloclassic® Cups CSF Cementless", Allopro AG, 1993.
Willert, "Zementiertes CF Hüft-endoprothesensystem mit zentrierhilfe", Allopro AG 1992 Switzerland.
Zweymüller, "Allopro Produktinformation—Alloclassic® Pfannen CSF Zementfrei", Allopro 1993.
Waldermar Link, Link® Ribbed System, Advertisement, Springer International / International Orthopaedics 1995.
Waldermar Link, "Link® Pressfit Acetabular Cup System", Advertisement, Springer International / International Orthopaedics 1994.
Aesculap AG, "PLasmacup, Cementless Acetabular Cup", Advertisement, Springer International / International Orthopaedics 1994.
The Journal of Bone and Joint Surgery, "The Furlong® H-A.C. Coated F.R.F. Acetabular Cup", Advertisement by Joint Replacement Instrumentation Ltd. 1995.
"Link® FGK-Acetabular Components", Advertisement, Acta Orthopaedica Scandinavica, May 1996.
Joint Replacement Instrumentation Ltd, Furlong® H-A.C. THR, Advertisement, The Journal of Bone and Joint Surgery, vol. 76-B, 1994.
"Argomedical", Advertisement, The Journal of Bone and Joint Surgery, vol. 76-B, 1994.
"Furlong® H-A.C." Advertisement by Joint Replacement Instrumentation Ltd., The Journal of Bone and Joint Surgery, vol. 76-B, 1994, No. 3 (May).
"BiContact", Advertisement by Aesculap, The Journal of Bone and Joint Surgery, vol. 76-B, 1994, No. 3 (May).
"Link® Lubinus SP II Anaatomically AdaptedTotal Hip System", Advertisements by Waldermar Link and ARG Medical, The Journal of Bone and Joint Surgery, vol. 76-B, 1994, No. Four (Jul.).
"Plus. the next generation", Advertisement, The Journal of Bone and Joint Surgery, vol. 76-B, 1994, No. Five (Sep.).
Böhm, et al., "Survival analysis of the Harris-Galante I acetabular cup", Eberhard-Karlss-Universitai, Tabingen, Germany, vol. 80-B, No. 3, May 1998.
Wilson, et al., "Acetabular Cup Dislocation: A New Complication of Total Joint Arthroplasty", AJR 151:133-134, Jul. 1988.
Cobb, et al., "The Elevated=Rim Acetabular Liner in Total Hip Arthroplasty: Relationship to Postoperative Dislocation", The Journal of Bone and Joint Surgery, vol. 78-A, No. 1, Jan. 1996.
Blömer, "3.2 Design Aspects of Modular Inlay Fixation", Mar. 8, 1997.
Simon, et al., Development and Validation of a Navigational Guidance System for Acetabular Implant Placement*, Apr. 1997.
Williams II, et al., "Fixation of Ultrahigh-molecular-weight Polyethylene Liners to Metal-backed Acetabular Cups", The Journal of Arthroplasty, vol. 12, No. 1, 1997.

Han, et al., "Lake Dissociation of the Polyethylene Liner from a Modular Acetabular Metal Shell after Primary Total Hip Arthroplasty", Yonsei Medical Journal, vol. 39, No. 3, pp. 277-282, 1998.
Gross, et al., "Revision Arthroplasty of the Acetabulum in Association with Loss of Bone Stock", The Journal of Bone and Joint Surgery, vol. 80-A, No. 3, Mar. 1998.
Shea, et al., "Wear of Non-Articulating Surfaces in Modular Acetabular Cups", American Society for Testing and Materials, Mar. 1997.
Barrack, et al., "Complications Related to Modularity of Total Hip Components", The Journal of Bone and Joint Surgery [Br], 1993; 75-B, 688-92.
Law, "Some landmarks in the surgery of the rheumatic diseases", Annals of the Royal College of Surgeons of England, vol. 61, 1979.
Swikert, et al., "Simulated Studies of Wear and Friction in Total Hip Prostheses Components with Various Ball Sizes and Surface Finishes", National Aeronautics and Space Administration, Mar. 1976.
Takahashi, "Follow-up study of the cup supporter (F-S type) in total hip replacement", Acta Medical Okayama, vol. 39, Issue 5, Article 7, Oct. 1985.
Simon, et al., "Catastrophic Failure of the Acetabular Component in a Ceramic-Polyethylene Bearing Total Hip Arthroplasty", The Journal of Arthroplasty, vol. 13, No. 1, 1998.
Barrack, "Modularity of Prosthetic Implants", J Am Acad Orthop Surg 1994:2:16-25.
Screen Shots of the Orthopaedic Division, Plasmacup®, Aesculap AG & Co., May 28, 1997.
Delaunay, et al., "Acetabular Screw Rings and Surface Treatment", Clinical Orthopaedics and Related Research, No. 340, pp. 130-141, 1997.
"Ringloc® Bi-Polar Articularing Hip System", Biomet Inc., 1997.
Brodner, et al., "Elevated Serum Cobalt with Metal-on-Metal Articulating Surfaces", J BoneJoint Surg [Br] 1997; 79-B:316-21.
"Furlong® H-A.C. Coated F.R.F. Acetabular Cup", Advertisement by Joint Replacement Instrumentation Ltd., The Journal of Bone and Joint Surgery, vol. 79-B, No. two (Mar.) 1997.
Screen Shots of the Orthopaedic Division, Plasmacup®, Aesculap AG & Co. May 1997.
Effenberger, et al. "X-ray criteria and radiological results of the Hofer-Imhof (H-I) threaded cup after primary implantation", J. Ortho. 135 (1997) 434-443.
Effenberger, et al., "Radiologische Verlaufskontrolle bei Primärimplantation mit der Hofer-Imhof-H/I)-Schrau bpfanne", ZB MED.
Hofer, et al., "Design und Operationstechnik der Hofer-Imhof-HI-Schraubpfanne", ZB MED 1993.
Hofer, et al., EN "Design and surgery technique of the Hofer-Imhof (H-I) threaded cup", ZMED.
Thabe, et al., "Mittelfristige Ergebnisse mit der zementfreien „Link-Endoprothese", Z. Orthop. 131 (1993) 568-573.
Gekeler, "Zementfrei implantieren mit der modularen sphärischen Press-fit-Pfanne", ZB MED, Implant Jan. 1998.
Täger, "Die SHEP-Prothese—Design und Anwendung", ZB MED.
Widmer, et al., "Kontaktfläche und Druckbelastung im Implantat-Knochen-Interface bei Press-Fit-Hüftpfannen im Vergleich zum natürlichen Hüftgelenk", Orthopade (1997) 26: 181-189.
Helfern, et al., "Zementfreie Pfanne und zementierter Schaft—Konzept einer „Hybrid-Lösung sowie Ergebnisse einer drei-bis sechsjährigen klinischen Erfahrung", Z. Orthop. 131 (1993) 578-584.
Thomsen, et al., "Werkstoffubersicht in der Hüftendoprothetik", Z. Orthop. 133 (1995) 1-4.
Thomsen, et al., "Zementlose Pfannenverankerung bei Hüftendoprothesen", Z. Orthop. 133 (1995) 551-557.
Friederich, et al., "5-bis 10-Jahresresultate zementfreier Hüft-Totalendoprothesen", ZB MED.
Hauser, et al., "Die Balgrist Hüftpfanne—Eine 4-bis 10-Jahres Überlebenszeitanalyse von zementfreien Hüftpfannen", Z. Orthop. 131 (1993) 585-593.
Grünther, et al., "Die isoelastische RM-Hüftendoprothese", Z. Orthop. 131 (1993) 539-542.

(56) References Cited

OTHER PUBLICATIONS

Boisgard, et al., "Failure of the polyethylene uncemented acetabular cup fixed onto the bone: study of 32 Freeman cups at an average of 9 years follow up", Revue de Chirurgie orthopedique, 1998, 84, 700-704.
Blömer, et al., "Überlegungen zum Pfannendesign Sphärisch oder konisch ? Gewinde selbstschneidend oder genchnitten ?", ZB MED.
Semlitsch, et al., "Titanlegierungen für zementlose Hüftendoprothesen", ZB MED.
Effenberger, et al., "Röntgenkriterien und radiologische Ergebnisse der Hofer-Imhof(H-I)-Schraubpfanne bei Erstimplantation", Z. Orthop. 135 (1997), 434-443.
Kutschera, et al., "Das zementfreie Zweymüller Hüft-System", Z. Ortho. 131 (1993) 513-517.
Koch, et al., "Kurzfristige Ergebnisse (2 bis 5 Jahre) der Hydroxylapatit-beschichteten Hüftendoprothesen vom Typ Furlong", Z. Orthop. 131 (1993), 562-.
Quack, et al., "Design Consideration to Improve the Acetabular Cup of the ESKA-THR System by Using the Wear Couple Ceramic-on-Ceramic", Biomedizinische Technik, Bank 41 Heft Sep. 1996 253-259.
Advertisement for merete MüllerCentric—Pfanne mit Abstandshalter, Z.Orthop. 136, 1998 Heft 6.
ESKA Implants, Hüft-Endoprothesensystem CL-Metallsockel, Advertisement, Urban & Vogel München Mar. 1997.
ESKA Implants, Hüft-Endoprothesensystem CL-Metallsockel, Advertisement, Urban & Vogel München Mar. 1997—English Version.
Protek, CLS—Das System, Advertisement, ZB MED, Operative Orthopädie und Traumatologie, Sep. 1989.
BiomEX L'Implant Cotyloïdien, Advertisement, Biomet, Revue de Chirurgie Orthopedique, vol. 81, 1995.
Catyle Espace B2C by Groupe Lépine, Advertisement, Revue de Chirurgie Orthopedique, vol. 83, Oct. 1997.
Cerafit by Ceraver Osteal, Advertisement, Revue de Chirurgie Orthopedique, vol. 83, Apr. 1997.
Cerafit by Ceraver Osteal, Advertisement, Revue de Chirurgie Orthopedique. vol. 84, May 1998.
Link® McMinn Acetabulum Rekonstruktionspfannen-System by Waldemar Link, Advertisement, Zeitschrift für Orthopädie und ihre Grenzgebiete.
Prothèse Totale de Hanche B2C by Groupe Lépine, Advertisement, Revue de Chirurgie Orthopedique, vol. 81, 1995.
Sikomet SM21®, Metall-Metall-Paarung by ENDO Plus, Advertisement, Operative Orthopädie und Traumatologie, 3, 1998.
Prothèse Totale de Hanche by Groupe Lépine, Advertisement, Revue de Chirurgie Orthopedique, vol. 84, Oct. 1998.
Link® Lubinus SPII, Advertisement, Revue de Chirurgie Orthopedique, vol. 84, Aug. 1997.
Catyle MBA by Groupe Lépine, Advertisement, Revue de Chirurgie Orthopedique, vol. 83, Jul. 1997.
Biolox forte by CeramTec, Advertisement, Orthopädie actuell/Z. Orthop., Heft 5 Band 135, Sep./Oct. 1997.
Gebauer, "The Cementless Cup in Total Hip Allo-arthroplasty—Analysis of Fixation Conditions in Different Models", Biomedizinische Technik, 1987.
Weber, "Metall-Metall-Totalprothese des Hüftgelenkes: Zurück in die Zukunft", Z. Orthop. 130 (1992) 306-309.
Waldemar Link Products, Advertisements, Zeitschrift für Orthopadie und ihre Grenzgebiete, May 1992 and May 1993.
Link® Pressfit-Hüftpfannen-System, Advertisement, Zeitschrift für Orthopädie und ihre Grenzgebiete, Mar./Apr. 1995.
Mectron® Titan Mecring® Zementfreies Acetabulum System by Mecron and S&G Huft-System by S&G Implants, Advertisement, Apr. 1987.
Iakovenko, et al., "Endoprosthesis of the hip joint with a prosthesis of up-to-date design", Vestn Khir Im II Grek.
Virabov, "Artificial demountable multipositional hip prosthesis", Orthop. Travmatol. Prot.
Saikko, et al., "Wear of the polyethylene acetabular cup", Acta Orthop Scand d1993; 64 (4):391-402.
Saikko, "Wear of polyethylene acetabular cups against alumina femoral heads", Acta Orthop Scand d1993; 64 (5): 507-512.
Saikko, "Wear of polyethylene acetabular cup", Acta Orthop Scandd 1995; 66 (6): 501-506.
Shirasaki, et al., "Biomechanical Study of Artificial Hip Joint", Transactions of the Japan Society of Mechanical Engineers, 1997.
Korzsh, et al., "A new acetabulum to the artificial hip joint of Sivash", Orthop. Travmatol. Prot.
Effenberger, "Röntgenkriterien und radiologische Ergebnisse der Hofer-Imhof (H-I)—Schraubpfanne bei Erstimplantation", Z. Orthop, 1997.
Movshovich, et al., "Experience with total endoprothesis of the hip joint using the first Soviet-made metal-polymer prosthesis", Orthop. Travmatol. Prot.
Sherepo, "A concept of need and construction of a hip joint prosthesis with isolation of the fraction point from the tissue", Med. Tekh.
Sherepo, "A shock-absorber-damper endoprosthesis for the hip joint", Med. Tekh.
Kuroki, "Artificial Hip Joints—Present and Future Development", Jinko Zouki.
Akamatsu, "Artificial Joints, a year's progress", Jinko Zouki.
Kondo, "Status of Bioceramics", Transactions of the Japan Society of Mechanical Engineers.
IMADE, "Artificial Joints, a year's progress", Jinko Zouki.
Boutin, "Arthroplastie totale de la hanche par prothèse en alumine frittée, Étude experimentale et premières applicaitons cliniques", Revue de Chirurgie Orthopédique, 1972, 58 3. pp. 229-246.
Therin, et al., "A histomorphometric comparieson of the muscular tissue reaction to stainless steel, pure titanium and titanium alloy implant materials", Journal of Materials Science; Materials in Medicine 2 (1991) 1-8.
Osorovitz, et al., "Résultats cliniques et radiographiques d'une série continue de 124 prothéses totales de hanche type Céraver-Ostéal avec courbe de survie á ans [Clinical and Radiographic Results of 124 Ceraver-Osteal Total Hip Arthroplasties]", Revue de Chirurgie Orthopédique, 1994.
Boutin, "Le frottement alumine-alumine en chirurgie de la hanche 1205 arthroplasties totales: Apr. 1970-Jun. 1980", Revue de Chirurgie Orthopedique, 1981, 67, 279-287.
Sedel, "L'alumine en chirurgie orthopédique", Cahiers D'enseignement de la SOFCOT, vol. 25 (1986), pp. 61-69.
Sedel, et al., "Alumina-on-Alumina Hip Replacement, Results and Survivorship in Young Patients", J Bone Joint Surg [Br] 1990; 72-B:658-63.
Lerouge, et al., "Ceramic-Ceramic and Metal-Polyethylene Total Hip Replacements", J Bone Joint Surg [Br] 1997; 79-B:135-9.
Kurtz, et al., "Contemporary Total Hip Arthroplasty: Hard-on-Hard Bearings and Highly Crosslinked EHMWPE", Elsevier Inc. / UHMWPE Biomaterials Handbook, Second Edition.
The Cerafit Cup, Product Information, Ceraver Osteal 1993.
The Cerafit Cup, Product Information, Ceraver Osteal 1995.
System 12 Designed to Address Issues of Acetabular Wear—Advertisement, The Journal of Bone and Joint Surgery, vol. 77-B (1995) No. 3 (May).
ABG II Acetabular Cup System, Advertisement, The Journal of Bone and Joint Surgery, vol. 78-B (1996) No. 6 (Nov.).
der Deutschen Gesellschaft für Unfallchirurgie e.V. 75 Jahre DGU, Nov. 19-22, 1997, Berlin.
Shetty, et al., Results of a hydroxyapatite-coated (Furlong) total hip replacement—a 13- to 15-Year Follow-Up, The Journal of Bone and Joint Surgery, vol. 87-B, No. 8, Aug. 2005.
Furlong, The Original Furlong® Hydroxyapatite Ceramic (Osprovit)® Coated Total Hip Replacement, Joint Replacement Instrumentation Ltd.
Biolox® Forte—The Gold Standard in Ceramics, CeramTec.
"Our Solution to the Problem Osteolysis: the Biolox® Forte Concept", CeramTec.
"Plasmacup SC", Aesculap.
"Das Resultat Praktischer Erfahrung: Schraubpfanne HI (int.pat.) nach Prof. Dr. H. Hofer, Salzburg", Intraplant/ Pentamedical.
"Die modulare Keramik-Gleitpaarung", Aesculap.

(56) References Cited

OTHER PUBLICATIONS

"S-Cup Produktinformation/Operationsanleitung", Biomet Merck.
"Modulare Pressfitpfanne MPF", Intraplant.
Samo Duofit®, Samo.
"Proximal-Press-Fit Das PPF Hüftendoprothesen-System", Pantitan.
"Variable Lösungen fur alle Anforderungen. Axis™—das modulare Hüftprothesen-System", Smith& Nephew.
"Ccontact SPH-Cup System Uncemented", Lima-Lto Medical Systems.
"Das Axis™-Hüftsystem", Smith & Nephew.
"Biolox® delta—A New Ceramic in Orthopaedics", CeramTec.
Boutin, "Les nouveaux matériaux utilisés dans les prothèses totales de hanche", Expansion Scientifique Francaise, 1979.
Toni, et al., "1.1 Ceramic-on-Ceramic: Long-Term Clnical Experience".
Toni, "Desisgn of the AN.C.A. Fit acetabular prosthesis", Rizzoli Orthopaedic Institute in Bologna.
Affatato, et al., "Usura metallo-RHWMPE: una prova sperimentale Metal-UHWMPE wear: experimental testing", Chir Organi Mov. LXXXII, 393-399, 1997.
Terzi, et al., "Fratture intraoperatorie del femore nei reimpiani protesici d'anca Intraoperative fractures of the femur in prosthetic hip reimplantations", Chir. Organi Mov. LXXXII, 221-229, 1997.
Toni, et al., "Hydroxyapatite as metallic prosthesis coating: preliminary clinical experience", Chir Organi Mov. LXXXI, 351-359, 1996.
Toni, et al., "The use of ceramic in prosthetic hip surgery. The state of the art", Chir Organi Mov LXXX, 125-137 1995.
"Le Cotyle "SC" "Titane-Back"—The "SC" Cup", Ceraver.
Scheller, et al., "1.8 MPF Modular Press Fit Cup—The Concept, Experience and First Results", Bioceramics in Hip Joint Replacement, Proceedings 5th International CeramTec Symposium Feb. 18/19, 2000.
"MPF—Modular Press-Fit Cup Short-Term Results of a Ceramic-on-Ceramic Bearing", Poster, University Hospital of Mannheim, Dec. 2002.
Effenberger, "Radiologische Ergebnisse der Hofer-Imhof-Hi-Schraubpfanne", W. Zuckschwerdt Verlag.
Programme ISIS by Tornier—Advertisement, Maitrise Orthopedique, Jan. 1993.
Chiropro GmbH Brochure, "Modulares Hüftprothesensystem zementiert zementfrei—Prebfitpfanne mit Zapfen PE—Inolay Keramik-Inlay".
Chiropro GmbH Brochure—EN Version, "Modular hip prosthesis system cemented—cement-free Press-fit socket with bolts PE inlay—ceramic inlay".
Cerafit by Ceraver Osteal—Advertisement, Maîtrise Orthopédique, 1993.
Articles and Advertisements, Advertisement, Maîtrise Orthopédique, Mar. 1993.
Protek, Advertisement, Maîtrise Orthopédique, Jun.-Jul. 1993.
Coctyle Harris Galante by Zimmer, Advertisement, Maîtrise Orthopédique, Sep. 1993.
Cupule Armor by Allopro, Advertisement, Maîtrise Orthopédique, Sep. 1994.
Atlas by FH, Advertisement, Maîtrise Orthopédique, Sep. 1994.
Advertisements, Maîtrise Orthopédique, Jan. 1998.
Cerafit Osteal by Ceraver Osteal, Advertisement, Maîtrise Orthopédique, Nov. 1994.
Aidlx® by ProthAid, Advertisement, Maîtrise Orthopédique, Nov. 1994.
ESOP-ALTAS by FH, Advertisement, Maîtrise Orthopédique, Jan. 1995.
Cupule Armor by Metasul, Advertisement, Maîtrise Orthopédique, Mar. 1995.
P.R.A. by FH, Advertisement, Maîtrise Orthopédique, Apr. 1995.
Articles and Advertisements, Maîtrise Orthopédique, Jun. 1995.
Articles and Advertisements, Maîtrise Orthopédique, Sep. 1995.
Articles and Advertisements—Maîtrise Orthopédique, Nov. 1995.
Articles and Advertisements—Maîtrise Orthopédique, Apr. 1996.
Articles and Advertisements—Maîtrise Orthopédique, Jun. 1996.
Articles and Advertisements—Maîtrise Orthopédique, Oct. 1996.
Articles and Advertisements—Maîtrise Orthopédique, Nov. 1996.
Articles and Advertisements—Maîtrise Orthopédique, Dec. 1996.
Articles and Advertisements—Maîtrise Orthopédique, Mar. 1997.
Articles and Advertisements—Maîtrise Orthopédique, Sep. 1997.
Articles and Advertisements—Maîtrise Orthopédique, Feb. 1998.
Articles and Advertisements—Maîtrise Orthopédique, Mar. 1998.
Articles and Advertisements—Maîtrise Orthopédique, May 1998.
Articles and Advertisements—Maîtrise Orthopédique, Jun. 1998.
Articles and Advertisements—Maîtrise Orthopédique, Sep. 1998.
Articles and Advertisements—Maîtrise Orthopédique, Oct. 1998.
Articles and Advertisements—Maîtrise Orthopédique, Nov. 1998.
Articles and Advertisements—Maîtrise Orthopédique, Dec. 1998.
Articles and Advertisements—Maîtrise Orthopédique, Jan. 1999.
Articles and Advertisements—Maîtrise Orthopédique, Feb. 1999.
Articles and Advertisements—Maîtrise Orthopédique, Mar. 1999.
Articles and Advertisements—Maîtrise Orthopédique, May 1999.
Topaze by Matco, Advertisement, Maîtrise Orthopédique,Dec. 1995.
Cotyle Nepturn by I.T.A.C., Advertisement, Maîtrise Orthopédique, Mar. 1996.
ALTO® by Merck Biomaterial, Advertisement, Maîtrise Orthopédique, Jan. 1997.
Biocontact® by Aesculap, Advertisement, Maîtrise Orthopédique, Feb. 1997.
Cotyle Press-Fit by Protek, Advertisement, Maîtrise Orthopédique, Apr. 1997.
Advertisements, Maîtrise Orthopédique, May 1997.
SL-Plus by Endo Plus, Advertisement, Maîtrise Orthopédique, Jun. 1997.
Atlas® by FH, Advertisement, Maîtrise Orthopédique, Oct. 1997.
Advertisements—Maîtrise Orthopédique—Nov. 1997.
Andigo® and Arpe® by Merck Biomaterial, Advertisement, Maîtrise Orthopédique, Dec. 1997.
Wolfhart, Die Keramikpaarung Biolox in der Hüftendoprothetik, Library records, proceedings des. 1 Cerasiv-Sysmposiums am Mar. 23, 1996 in Stuttgartt.
Wolfhart, "Die Keramikpaarung Biolox in der Hüftendoprothetik" Library Catalog Records, am Mar. 23, 1996 in Stuttgart; 31 Tabellen.
Wolfhart, "Performance of the wear couple Biolox forte in hip arthroplasty proceedings of the 2nd Symposium on Ceramic Wear Couple", Library Records, Mar. 8, 1997 Stuttgart (Germany); 42 Tabellen.
Wolfhart, "Bioceramics in orthopaedics new applications", library records, proceedings of the 3rd Intern ational Symposium on Ceramic Wear Couple, Feb. 14, 1998 Stuttgart (Germany); 24 tables.
Wolfhart, "Bioceramics in orthopaedics: new applications", library records. proceedings of the 3rd International Symposium on Ceramic Wear Couple, Feb. 14, 1998, Stuttgart (Germany).
ANCA-Fit Brochure and Surgical Guide Tender, Elenco Documentazione Lotto N. 5, Cremascoli Ortho Group, Oct. 1997.
ANCA-Fit Product Information, Cremascoli Ortho Group, Mar. 26, 1999.
ANCA-Fit Surgical Technique, Cremascoli Ortho Group.
Toni, et al., "Anatomic cementless total hip arthroplasty with ceramic bearings and modular necks: 3 to 5 years follow-up", Wichtig Editore / Hip International, vol. 11, No. 1, 2001, pp. 1-17.
Toni, et al., "Cementless hip arthroplasty with a modular neck", Chir. Organi Mov. LXXXVI, 73-85, 2001.
Alessandrini, et al., "Follow-Up Results with GSP and ANCA Fit Uncemented Prostheses", Ospedale Civile, Piacenza, 1993.
"Variall™ Pfanne—Die innovative Weiterentwicklung der bewahrten konischen schraubpfanne, Produktinformation und Operationsstechnik", Sulzer Orthopedics Ltd., 2000.
"Variall™ Pfanne—Die innovative Weiterentwicklung der bewahrten konischen schraubpfanne, Produktinformation und Operationsstechnik", Sulzer Orthopedics Ltd., 2000—English Version.
"Thompson Hip Prosthesis", Cremascoli Ortho Group, Jan. 21, 1997.
CeramTec Medical Products Divisison—The latest News, CeraNews, Nov. 1994.

(56) References Cited

OTHER PUBLICATIONS

Goodman, et al., The Fibrous Tissue Interface Surrounding Well-Fixed, Revised, Cementless Acetabular Components for Hip Replacement, ASTM/Modularity of Orthopedic Implants, Mar. 1997, pp. 21-32.
Shea, et al., "Wear of Non-Articulating Surfaces in Modular Acetabular Cups", ASTM/Modularity of Orthopedic Implants, Mar. 1997.
Lambert, et al., "Test Method Comparing Torsional Fatigue of Modular Acetabular Components", ASTM/Modularity of Orthopedic Implants, Mar. 1997.
Fosco, et al., "The Importance of Fatigue Loading When Assessing Liner/Shell Distraction Resistance andCongruency for Modular Acetabular Components", ASTM/Modularity of Orthopedic Implants, Mar. 1997.
Semlitsch, et al., "Implant materials for hip endoprostheses: old proofs and new trends", Arch Orthop Trauma Surg (1995) 114:61-67.
Buchanan, Experience with Furlong® H-A.C. Coated Implants in T.H.R., Furlong Research Foundation, Nov. 1995, pp. 127-134.
Rueda, "The Spanish Clinical Experience", Hydroxyapatite Ceramic a Decade of Experience in Hip Arthroplasty, Nov. 2 and 3, 1995, Furlong Research Foundation, pp. 227-234.
Rieger, "Ceramic Bearing Surfaces in Hip Arthroplasty", Hydroxyapatite Ceramic a Decade of Experience in Hip Arthroplasty, Nov. 2 and 3, 1995, Furlong Research Foundation, pp. 239-254.
Walker, "Secured Fixation of Threaded Cups with H-A.C.", Hydroxyapatite Ceramic a Decade of Experience in Hip Arthroplasty, Nov. 2 and 3, 1995, Furlong Research Foundation, pp. 255-266.
Clarke, Role of Ceramic Implants, Design and Clinical Success with Total Hip Prosthetic Ceramic-to-Ceramic Bearings, Clnical Orthopaedics and Related Research, Sep. 1992, pp. 19-30.
Axis I, Product Information, Implantat-ATlas, Jan. 2002.
Artroprotesi totali dell'anca, Stratec Medical, Jan. 2001.
"The S-Rom™ Total Hip System", Joint Medical Product Corporation, Nov. 1990.
"Protesi Totale Dell'Anca Furlong® H-A.C.", Joint Replacement Instrumentation Ltd.
Duofit®, Samo, Apr. 1996.
SPH System—86th Congresso Nazionale Societa Italiana di Ortopedia e Traumatologia, Rome (Italy) Nov. 13, 2001, Lima-Lto.
RM Cups fro cementless fixation, RM Isoelestic-Joints.
AN.C.A. The Evolution of Anatomical Design in the Respect of Biocompatibility, G. Cremascoli.
ANCA-Fit Technica Operatoria, Cremascoli Ortho Group.
Protesi Autocentrante Universale in Titanio tipe Charnley-Müller, G. Cremascoli.
A.H.S. Artroprotesi Cementata Sistema Universale, G. Cremascoli.
JVC Brochure, G. Cremascoli.
PTCR-E Brochure, Cremascoli Ortho Group.
MRL Cemented Prosthesis Universal System, G. Cremascoli.
Vives, Contact II Technique D'Implantation, G. Cremascoli.
Vives, Prothese Contact II, G. Cremascoli.
GCO Protesi Senza Cemento, G. Cremascoli.
Titan™ Total Hip System, Dow Corning Wright, 1983.
BDH Total Hip System, Intermedics Orthopedics Inc., Jan. 1983.
The Titanium Aufranc-Turner A.T.S. Press Fit Total Hip System, Howmedica.
Willert, "The CF Cemented Total Hip System With Centering Guide" Product Information, Allopro AG, 1992.
Willert, "The CF Cemented Total Hip System With Centering Guide" Product Information, Allopro AG, 1993.
Biolox forte® : Biolox forte® "unmeasurable degree of abrasion", Cerasiv GmbH.
ALBI+Cup, Cremascoli Ortho Group.
ANCA Fit Cup With Holes HA Coated, Cremascoli Ortho Group.
ANCA Fit Cup W/Out Holes HA Coated, Cremascoli Ortho Group.
ANCA Fit Cup With Holes Not HA Coated, Cremascoli Ortho Group.
ANCA Fit Cup Without Holes Not HA Coated, Cremascoli Ortho Group.
ANCA Fit Cup HA Coated With Holes No Fins, Cremascoli Ortho Group.
ANCA Fit Cup With Holes No Fins, Cremascoli Ortho Group.
OLBIA Implant Cotyloidien Sans Ciment, Zimmer.
OLBIA Cup, Cremascoli Ortho Group.
Cotyle H.AP.
OLBIA Cup HA Coated, Cremascoli Ortho Group.
TFM
OLBA Cup HA Coated, Cremascoli Ortho Group.
TMF Cotyle Revetu d'Hydroxyapatite.
E.H.S. Acetabular Cup HA Coated, Cremascoli Ortho Group.
Procotyl, Cremascoli Ortho Group.
TMF Acetabular Cup, Cremascoli Ortho Group.
C-Card Acetabular Cup, Cremascoli Ortho Group.
Cotyle Demi-spheriques Impacte en Titane d'Epaisseur Minimum.
Polyethylene Acetabular Cup, Cremascoli Ortho Group.
Orthopädie 5 and ihre Grenzgebiete, Biolox Advertisement, Zeitschrift für Orthopädie, 135, 1997.
Cup Cupole Acetabular Cup, Cremascoli Ortho Group.
Maestro-Polyethylene Cup (Type "Müller", Cremascoli Ortho Group.
Rnoht Cup (Type Müller), Cremascoli Ortho Group.
Les Cotyles Cerafit by Cerafit Osteal—Advertisement, Revue de Chirurgie Orthopedique, Oct. 1998.
Vives Polyethylene Cup, Cremascoli Ortho Group.
ALBI+Cup Without Holes Not HA, Cremascoli Ortho Group.
Cerasiv's answser to the problem of osteolysis: The Biolox/ Biolox sliding combination, CeraNews, Mar. 1996, Edition 3.
Saikko, "Wear of alumina-on-alumina total hip joints studied with a hip joint simulator—Part I. The one million cycle test". Cerasiv GmbH, Sep. 25, 1996.
Biolox® forte—A pair of sliding champions!, Cerasiv GmbH.
Medical Surface Engineering—Coating service for medical products, Cerasiv GmbH.
ANCA-Fit, Cremascoli Ortho Group.
AN.C.A. Fit Cup with Holes, Cremascoli Ortho Group.
AN.C.A. Fit Cup Without Holes, G. Cremascoli.
McTighe, et al., "20—Design Considerations for Cementless Total Hip Arthroplasty", Marcel Dekker, Inc., 1995, pp. 3-42.
Kuhn, et al., "Initial Stability of Press-fit Acetabular Cups. In vitro Lever-out Trials", Biomedizinische Technik Dec. 1999.
Decking, et al., Proximate Verankerung von Hüft-Endoprothesen mit poröser Oberfläche: 6-Jahres-Ergebnisse, Z. Orthop 137 (1999) 108-113.
Delaunay, et al., "Survie a 10 ans des protheses totales de Zweymuller en arthroplastie primaire non cimentee de hanche—Ten year survivorship of the Zwweymuller prosthesis in cementless primary total hip arthroplasty", Revue de Chirurgie Orthopedique, Sep. 1998.
Wessinghage, et al., "Langzeitergebnisse nach zementierten Hüft-Totalendoprothesen bei chronischen Polyarthritiden", Orthopäde 1998, 27-381-391 Springer-verlag 1998.
Effenberger, et al., "Zementfreie Hüftendoprothetik bei Patienten mit rheumatoider Arthritis", Orthopade 1998, 27:354-365—Springer-verlag 1998.
Echtler, et al., "8-Year Survivorship Analysis and Subjective Results of 687 Primary Balgrist Hip Sockets", Acta Orthopaedica Belgica, vol. 65—Mar. 1999.
Evora® by SEM, Advertisement, Revue de Chirurgie Orthopedique, Nov. 1999.
Modulaire Biconique Anatomique by Groupe Lepine, Revue de Chirurgie Orthopedique, Mar. 1999.
Kinner, et al., "Erfahrungen mit einer Hydroxylapatit-beschichteten, makroporös strukterierten Hüftendoprothese", Z. Orthop. 137 (1999) pp. 114-121.
Syrakas, Inaugural Dissertation—"Mittel-und Langzeitergebnisse bei totalendoprothetischem Hüftgelenkersatz nach Zweymüller", ZB MED.
Henpge, "3.1 Analyse der Fehlergebnisse der Keramik-Keramik-Gleitpaarung", Die Keramikpaarung Biolox in der Hüftendoprothetik, Proceedings des 1. Cerasiv-Symposiums am Mar. 23, 1996 Stuttgart.

(56) References Cited

OTHER PUBLICATIONS

Plasmacup® by Aesculap Orthopaedics, Advertisement, Springer/Implant.
MptlerCentric™ by Merete, Zeitschrift für Orthopädie, Sep./Oct. 1998.
Biolox® forte by CeramTec, Advertisement, Zeitschrift für Orthopädie, Mar./Apr. 1999.
Cerafit by Ceraver Osteal, Advertisement, Revue de Chirurgie Orthopedique, May 1998.
Jubel, et al., "Tips and Tricks Entfernung eines Metasul-Inlays® beim Hüftpfannenwechsel", Operative Orthopädie und Traumatologie, 1998, pp. 157-158.
Wagner, et al.—"German Clinical Results with Metasul Bearings", Hans Huber/Metasul a Metal-on-Metal Bearing, 1999, pp. 170-191.
Dorr, et al. Metasul Metal-on-Metal Articulation: Five Year Results, Hans Huber/Metasul a Metal-on-Metal Bearing, 1999, pp. 191-196.
Bergmann, et al., "1.8 The Rationale, Short-term Outcome and Early Complications of a Ceramic Couple in Total Hip Arthroplasty", Georg Thieme Verlag/Reliability and Long-term Results of Ceramics in Orthopaedics, 1999.
Sedel, "Evolution of Alumina/Alumina Implants", Georg Thieme Verlag/Reliability and Long-term Results of Ceramics in Orthopaedics, 1999.
Goossens, "1.3 The Transcend Alumina Ceramic Hip Articulation System—Surgical Technique—Preliminary Results of 51 cases", Georg Thieme Verlag/Reliability and Long-term Results of Ceramics in Orthopaedics, 1999.
Sikomet SM 21® by Endo Plus, Advertisement, Operative Orthopädie und Traumatologie, Mar. 1998.
Ultima® Schraubpfanne by Johnson & Johnson, Advertisement, Operative Orthopädie und Traumatologie, Mar. 1998.
Blömer, "Biomechanical aspects of modular inlay fixation", Wichtig Editore/Hip International.
"Reflection I & FSO Porous-Coated Acetebular Component Surgical Technique", Smith & Nephew, Apr. 1997.
"Reflection I and V Porous-Coated Acetabular Component Surgical Technique", Smith & Nephew, Jul. 1995.
Willmann, "Fretting of Modular Implant Systems", Biomedizinische Technik, 1993.
Bosdorf, et al., "Materials for Hip Joint Prostheses—Alaternatives to Standard Materials", Biomedizinische Technik, 1995.
Böhler, "Evolving Technologies: New Answers or New Problems? Metal/Metal Articulating Interfaces", Orthopedicss, Sep. 1995 vol. 18, No. 9, pp. 879-880.
Böhler, "Comparieson of Migration in Modular Sockets with Ceramic and Polyethylene Inlays", Orthopedics, Dec. 2000, vol. 23, No. 12, pp. 1261-1266.
Nakamura, "Bioceramics in Orthopedic Surgery", Bioceramics; proceedings of the International Symposium on Ceramics in Medicine, vol. 9, 1996, pp. 31-34.
Wolfhart, Library Catalog Records Regarding "Die Keramikpaarung Biolox in der Huftendoprothetik" am Mar. 23, 1996, Stuttgart, 31 Tabellen.
Wolfhart, Library Catalog Records Regarding "Performance of the war couple Biolox forte in hip arthroplasty" proceedings of the 2nd Symposium on Ceramic Wear Couple, Mar. 8, 1997, Stuttgart, 42 Tabellen.
Wolfhart, Library Catalog Records Regarding "Bioceramics in orthopaedics new applications"; proceedings of the 3rd International Symposium on Ceramic Wear Couple, Feb. 14, 1998, Stuttgart.
Protek, "Cementless Acetabulum Replacement St. Nabor", Brochure 1990.
"Omnifit® Hip System", Brochure, Osteonics Corp., 1986.
"Addressing the Acetabular Crisis", Brochure, DePuy, Jan. 1991.
"Arthopor™ Oblong Cups for Acetabular Defects", Advertisement, Joint Medical Products Corporation, JBJS, Jul. 1995.
Maloney, et al., "Specific Identification of Cementless Acetabular Components Prior to Revision Surgery", A scientific exhibited presented at the 64th Annual Meeting of the American Academy of Orthopaedic Surgeons, Feb. 13-17, 1997, San Francisco, CA.
Brehm, "MRS-Titan Modular Revision Staycup", May 1996.
"Ringloc® Acetabular Series the Standdard by Which All Others are Judged", Biomet, JBJS, May 1995.
APR™ Universal Hip System with Cancellous-Structured Titanium™, Intermedics Orthopedics Inc., May 1987.
"Premier-Total™ Hip System", Intermedics Orthopedics, Inc.™, a Company of Sulzermedica, 1988.
"The CLS Uncemented Total Hip Replacement System", Protek, Jan. 1991.
"Self-Aligning Modular-Bipolar Hip Prosthesis", Protek, Jan. 1990.
Self-Locking System SLS-88, Protek, 1991.
"System® 12 Acetabular Components", Howmedica, 1995.
"Osteolock™ Acetabular Components", Howmedica, 1993.
Terzi, et al., "The ceramic-ceramic hip prosthesis: 1000 implants in ten years", Abstracts from II Meeting of the Italian Hip Society (COXA)—Bologna, IT, Nov. 28, 1997 (Hip International 1998: 8: 31-37.
Witvoét, et al., "Total hip arthroplasty with a titanium threaded cup. Survivorship analysis of 508 cups", Revue de Chirurgie Orthopedique, 1993, 79, 542-552.
Witvoét, et al., "Total hip arthroplasty with a titanium threaded acetabular ring. Outcome of 446 prostheses with an average fofllow-up time of 4 years", EN Version—Revue de Chirurgie Orthopedique, 1993, 79, 542-552.
Bläsius, et al., "Hüftpfannen: Verankerungstechniken und Pfannenwanderung", Springer/Implant, 1995-1996, pp. 1-6.
Aktuelle Trends der Hüftpfannen-Implantation, Springer/Implant, 1995-1996, pp. 9-11.
Witvoet, "Arthroplastie Total De Hanche Avec Anneau Cotyloiden En Titane Visse", Revue de Chirurgie Orthopedique dt Reparatrice de, 1993.
Böhler, et al., "Ergebnisses mit der Keramik-Keramik-Gleitpaarung in der Hüftendoprothetik", Die Keramikpaarung Biolox in der Hüftendoprothetik, Proceedings des 1. Cerasiv-Symposiums am Mar. 23, 1996 Stuttgart.
Mittelmeier, et al., 1.3 Entwicklung und 20 Jahre klinische Erfahrung mit Keramik-Hüftendoprothesen (bei über 4000 Fällen), Die Keramikpaarung Biolox in der Hüftendoprothetik, Proceedings des 1. Cerasiv-Symposiums am Mar. 23, 1996 Stuttgart.
Lintner, et al., "2.2 Morphologisch-morphometrische Untersuchungen zum Einbauverhalten keramischer Pfannen und deren Partikelfreisetzung", Die Keramikpaarung Biolox in der Hüftendoprothetik, Proceedings des 1. Cerasiv-Symposiums am Mar. 23, 1996 Stuttgart.
Willmann, et al., "Ceramic Cups for Total Hip Replacement Part 5: Consideration of Designs", Biomed Technology 43 (1998), 342-349.
Willman, et al., "Ceramic Cups for Total Hip Replacement Part 5: Consideration of Designs", Biomed Technology 43 (1998), 342-349 English Translation.
Stock, "Die Langzeiterfahrung mit Al2O3-Keramikgleitpaarungen an der Hüfte seit 1974", Die Keramikpaarung Biolox in der Hüftendoprothetik Proceedings des 1. Cerasiv-Sumposiums am 23, M1996 in Stuttgart.
Pförringer, "Überlastbarkeit hüftendoprothetisch versorgter Patienten", Die Keramikpaarung Biolox in der Hüftendoprothetik Proceedings des 1. Cerasiv-Sumposiums am 23, M1996 in Stuttgart.
Krohn, "4.1 Qualitätsmanagement von keramischen Hüftgelenkimplantaten", Die Keramikpaarung Biolox in der Hüftendoprothetik Proceedings des 1. Cerasiv-Sumposiums am 23, M1996 in Stuttgart.
Pfaff, "Herstellung von Keramikkomponenten für die Endoprothetik", Die Keramikpaarung Biolox in der Hüftendoprothetik Proceedings des 1. Cerasiv-Sumposiums am 23, M1996 in Stuttgart.
Baur, "Das Konzept „Metall-Metall-Artikulation beim künstlichen Hüftgelenksersatz", Performance of the Wear Couple Biolox forte in Hip Arthroplasty, Proceedings of the 2nd Symposium on Ceramic Wear Couple Mar. 8, 1997 Stuttgart (Germany).
Maaz, et al., 'Erfahrungen mit dem Kaiserswerther Pfannen-system (Metallschraubring mit Keramikinlay), Performance of the Wear Couple Biolox forte in Hip Arthroplasty, Proceedings of the 2nd Symposium on Ceramic Wear Couple Mar. 8, 1997 Stuttgart (Germany).

(56) References Cited

OTHER PUBLICATIONS

Stock, Long-term Experience with A1203 Ceramic-on-Ceramic Combinations at the Hip since 1974, Proceedings of the Cerasiv Symposium on Mar. 23, 1996, in Stuttgart.

Böhler, et al., "3.2 Ergebnisse mit der Keramik-Keramik-Gleitpaarung in der Hüftendoprothetik", 1st Biolox Symposium.

Widhalm, et al., "Die Variopfanne mit Preβfitverankerung und Keramik-Gleitpaarung. Konzept und erste Ergebnisse", Performance of the Wear Couple Biolox forte in Hip Arthroplasty, Proceedings of the 2nd Symposium on Ceramic Wear Couple Mar. 8, 1997 Stuttgart (Germany).

Menge, et al., "2.11 Mittelfristige Ergebnisse mit dem SI-Schraubring mit Keramik-Inserts", Performance of the Wear Couple Biolox forte in Hip Arthroplasty, Proceedings of the 2nd Symposium on Ceramic Wear Couple Mar. 8, 1997 Stuttgart (Germany).

Lubinus, 2.12 Das Konzept des funktionsgeschützten Keramiklagers (FGK), Performance of the Wear Couple Biolox forte in Hip Arthroplasty, Proceedings of the 2nd Symposium on Ceramic Wear Couple Mar. 8, 1997 Stuttgart (Germany).

Willmann, 3.7 Wie darf man keramische Komponenten für Hiiftendoprothesen sterilisieren?, Performance of the Wear Couple Biolox forte in Hip Arthroplasty, Proceedings of the 2nd Symposium on Ceramic Wear Couple Mar. 8, 1997 Stuttgart (Germany).

Gekeler, "1.7 Sphärische Press-fit-Pfannen und erste Klinische Erfahrungen mit der Keramik-Gleitpaarung. (Plasmacup SC)", Bioceramics in Orthopaedics—New Applications, Proceedings of the 3rd International Symposium on Ceramic Wear Couple, Feb. 14, 1998 Stuttgart (Germany)

Niedhart, et al., "Klinische Anforderungen an Knochenersatzstoffe", Bioceramics in Orthopaedics—New Applications, Proceedings of the 3rd International Symposium on Ceramic Wear Couple, Feb. 14, 1998 Stuttgart (Germany).

Dietz, et al., "2.2 Osteoinductal®—neuer Knochenersatzstoff als osteogenetische, entzündungshemmende und bakteriostatische Knochenwundabdeckung", Bioceramics in Orthopaedics—New Applications, Proceedings of the 3rd International Symposium on Ceramic Wear Couple, Feb. 14, 1998 Stuttgart (Germany).

Scholz, et al., "2.3 Die Auffüllung von osteolytischen Knochendefekten mittels Osprovit—Korngröβe 2,5-3,15 mm", Bioceramics in Orthopaedics—New Applications, Proceedings of the 3rd International Symposium on Ceramic Wear Couple, Feb. 14, 1998 Stuttgart (Germany).

Hein, et al., "2.5 Hydroxylapatit in der Hüftendoprothetik", Bioceramics in Orthopaedics—New Applications, Proceedings of the 3rd International Symposium on Ceramic Wear Couple, Feb. 14, 1998 Stuttgart (Germany).

Jerosch, "3.2 Aktueller Stand in der Schulterendoprothetik—Mögliche Indikationen für die Verwendudng von Keramik", Bioceramics in Orthopaedics—New Applications, Proceedings of the 3rd International Symposium on Ceramic Wear Couple, Feb. 14, 1998 Stuttgart (Germany).

Hennig, et al., "3.3 Ein neues Konzept für die bipolare Prothese", Bioceramics in Orthopaedics—New Applications, Proceedings of the 3rd International Symposium on Ceramic Wear Couple, Feb. 14, 1998 Stuttgart (Germany).

Puhl, et al., "4.4 Standortbestimmung Knieendoprothetik in Europa", Bioceramics in Orthopaedics—New Applications, Proceedings of the 3rd International Symposium on Ceramic Wear Couple, Feb. 14, 1998 Stuttgart (Germany).

Fuchs, et al., "First 2-years results of single designed cemented and noncemented BF prosthesis in total hip arthroplasty" The Orthopedic Journal of China—vol. 6 pp. 711-715, 1999.

MetaSUL Brochure, Protek: SulzerMedica.

Franke, et al., "Monolithische versus modular augfebaute, zementfreie Keramik-Hüft-Endoprothesen", Proceedings of the 2nd Symposium onCeramic Wear Couple Mar. 8, 1997 Stuttgart Germany.

Franke, et al., Monolithic versus modularly designed, cement-less ceramic hip endoprosthes, Proceedings of the 2nd Symposium onCeramic Wear Couple Mar. 8, 1997 Stuttgart GermanyEN.

Aesculap Orthopaedics Brochure.

Hendrich, et al., 1.7 Klinische Erfahrungen and Migrationsanalyse—Plasmacup, Clinical Experience with Ceramics in Total Joint Replacement, 5th Biolox Symposium, pp. 26-34.

Gekeler, "Zementfrei Implantieren Mit Der Modularen Sphärischen Press-fit-Pfanne", Aesculap.

Plasmacup Product Information, Aesculap.

Quack, "Design Consideration to Improve the Acetabular Cup of the ESKA-THR System by Using the Wear Couple Ceramic-on-Ceramic", Biomedical Engineering, vol. 41, Issue Sep. 1996 pp. 253-259.

Das Hybridsystem, Ceraver Osteal Brochure, 1994.

Hofer, "10 Years with the Hofer-Imhof-(HI)-Threaded Cup", EN, Compendium of the Symposium , Apr. 25, 1998, Salzburg.

Axis Cup Image, Smith & Nephew.

Hofer, 10 Jahre Hofer-Imhof-(HI)-Pfanne, Kompendium des Symposiums vom Apr. 25, 1998 in Salzburg.

Kummer, "Spannungsverteilung im Knöchernen Lager zementfreier Hüftendoprothesenpfannen mit besonderer Berücksichtigung der Hofer-Imhof-Pfanne", Kompendium des Symposiums vom Apr. 25, 1998 in Salzburg.

Blaschke, et al., "Lanagzeitergebnisse der Hofer-Imhofpfanne", Kompendium des Symposiums vom Apr. 25, 1998 in Salzburg, pp. 31-40.

Maronna, et al., "8 Jahre Erfahrung mit der HI-Pfanne", Kompendium des Symposiums vom Apr. 25, 1998 in Salzburg, pp. 41-47.

Zichner, "Hofer-Imhof-Pfanne, Wanderungsverhalten und Knochendicchtegehalt mittels ERBA u. DEXA", Kompendium des Symposiums vom Apr. 25, 1998 in Salzburg, pp. 49-50.

Peyer, et al., "Luzerner Erfahrungen mit der HI-Pfanne", Kompendium des Symposiums vom Apr. 25, 1998 in Salzburg, pp. 51-53.

Wagner, et al., "Die Versorgung der Dysplasiecoxarthrose mit der Hofer-Imhof Pfanne plus Pfannendachplastik", Kompendium des Symposiums vom Apr. 25, 1998 in Salzburg, pp. 55-58.

Dorn, et al., "Die Metall / Metall Gleitkombination zur HI-Pfanne", Kompendium des Symposiums vom Apr. 25, 1998 in Salzburg, pp. 59-62.

Dorn, et al., "The Metal-on-Metal Sliding Combination Concerning for the HI Socket", Compendium of the Symposium, Apr. 25, 1998, Salzburg.

Hofer, "Hofer-Imhof (H-I) CE/CE", Intraplant AG, 1996.

Hofer, "Hofer Imhof (H-I) ME/ME", Intraplant AG, 1995.

Hofer, Operations-Technik Schraubpfanne HI (int. pat.), Intraplant AG.

Hofer, "Surgery technique H-I threaded cup (int.pat)", EN, Intraplant.

HI Cup Symposium—15 Jahre Jubilaum der HI-Pfanne—Abstracts, Intraplant AG, May 23, 2003.

"GSS—Pressfit—Pfanne", Internal Document, Intraplant AG, Jan. 20, 1998.

Zweymüller, "Bicon Plus", Brochure, Plus Endoprothetik, 1993.

Cerafit, "3 mois post-op", Product Information, Ceraver Osteal.

"Das SI—Hüftpfannenn—System Type Kaiserswerth", Implant-Service.

Witvoët, "Total hip arthroplasty with a titanium threaded acetabular ring. Outcome of 446 prostheses with an average follow-up times of 4 years", Revue de Chirurgie Orthopédique 1993, 79, 542-552.

Willmann, et al., "Ceramic Acetabular Cups for Total Hip Replacement Part 2: Component Testing and Reliability", Biomedizinische Technik, Oct. 1996.

Willmann, et al., "Ceramic Cup Inserts for Hip Endoprostheses", Biomedizinische Technik, 1996.

Willmann, et al., "Ceramic Cup Inserts for Hip EndoprosthesesEN", Biomedizinische Technik, 1996.

Ceranews Special, "Biolox® -Implantate im klinischen Einsatz", Sep. 1994.

Ceranews, Cerasiv's Antwort auf das Problem der Osteolyse: Die Gleitpaarung Biolox/Biolox®, Mar. 1996.

(56) References Cited

OTHER PUBLICATIONS

Ceranews Special Edition, Nov. 1996.
Bädorf, et al., Klinische Fakten zur Gleitpaarung Keramik / Keramik, Cerasiv.
Effenberger, et al., Zementfreie Hüftpfannen, Implantat-Atlas, Publication, MCU 2002.
Effenberger, "Aktueller Stand zementfreier Hüftpfannen".
Wintermantel, et al., "Medizintechnik—Life Science Engineering", Springer, 2009.
Buchhorn, et al., "Tehcnical Principles, Design and Safety of Joint Implants", Hogrefe & Huber Publishers, 1994.
"The Original Furlong® Hydroxyapatite Ceramic (Osprovit)® Coated Total Hip Replacement", Furlong® H-A.C. Femur Schäfte, Nov. 1997.
"The Original Furlong® Hydroxyapatite Ceramic (Osprovit)® Coated Total Hip Replacement", Furlong® Vastagos Femorales H-A. C., MBA.
Lord Madreporique®, Brochure, Howmedica.
Furlong, "Protesis Total de Cadera", Joint Replacement Instrumentation Ltd.
"Hooded Inserts for Furlong H-A.C. C.S.F. Cups", Joint Replacement Instrumentation Ltd., 1993.
Sedel, et al., "Prostaglandin E2 level in tissue surrounding aseptic failed total hips", Archives of Orthopaedic and Trauma Surgery, Sep. 1992.
Sedel, et al., "La Prothese Totale De Hanche Avant 50 Ans", Revue du Rhumatisme et des Maladies Osteo-Articulaires, 1990.
Witvoët, et al., "Total hip arthroplasty with a titanium threaded cup. Survivorhip analysis of 508 cups", Revue de Chirurgie Orthopedique 1993, 79, 542-552.
Witvoët, et al., "Total hip arthroplasty with a titanium threaded cup. Survivorhip analysis of 508 cups", Revue de Chirurgie Orthopedique 1993, 79, 542-552—Better version without cover page.
"Technique de Mise en Place D'un Cotyle Sans Ciment Ceraver S.C.".
Boutin, "Evolution De L'Arthroplastie Sans Ciment a Vec Le Couple Alumine-Alumine Et L'Alliage De Titane (1971-1984)", Annales Orthopediques de lQuest.
Boutin, "Les nouveaux matériaux utilisés dans les prothèses totales de hanche", SOFCOT, 1979, pp. 27-44.
Dorlot, et al—"La Prothese 'SC' Sans Ciment the 'SC' Cementless Prosthesis", John Wiley & Sons Inc./J. Biomed. Mater. Res: Applied Biomaterials,, 1989.
"Anatomiques Osteal—Les Prostheses Qui Reparatissent et Transmettent les Contrainates a IOs", Ceraver.
Photographs "A" and "A2" Ceraver Osteal Metal Acetabular Shell and Ceramic Insert (having self locking mating tapers).
Photographs B of Ceraver Osteal Acetabular Shell, Insert and Ball, Ceraver.
Howmedica, Evolution PCA® Hip System, Oct. 27, 1998.
Zeller, et al., "Das Prothesensystem "Vektor"—anisotrop elastische Pfanne and Spiral-Schaff", ZB MED.
Trident Ad, 1996.
Saikko, et al., "Wear of the polyethylene acetabular cup Metallic and ceramic heads compared in a hip simulator", Acta Orthop Scand 1993; 64 (4):391-402.
Ray, "Survie à plus de 15 ans de prothèses métal de Mac-Kee Farrar a propos de 58 observations et de 4 cupules explantées" Survival beyond 15 years of metal-metal Mac-Kee Farrar hip prostheses, Revue de Chirurgie Orthopédia 1996, 82, 85-89.
Quack, et al., "Weiterentwicklung des ESKA-Spongiosametall-Pfannensystems durch die Biolox forte Gleitpaarung", Proceedings of the 2nd Symposium on Ceramic Wear Couple Mar. 8, 1997 Stuttgart (Germany).
Quack, et al., "Weiterentwicklung des ESKA-Spongiosametall-Pfannensystems durch die Biolox forte Gleitpaarung", English Translation, Proceedings of the 2nd Symposium on Ceramic Wear Couple Mar. 8, 1997 Stuttgart (Germany).

Plus Orthopedics, Design-Unterschiede der verschiedenen HI™ Schalen-Typen und passende Instrumente dazu (für Revisionen), Apr. 2005.
Matsui, et al., "The Metal-Cancellous Cementless Lübeck total hip arthroplasty Five-to-Nine Year Results", The Journal of Bone and Joint Surgery 1998;80-B:404-10.
Lieberman, et al., "Wear of the Polyethylene Liner-Metallic Shell Interface in Modular Acetabular Components", The Journal of Arthroplasty, vol. 11 No. 5 1996.
Jubel, et al., "Entfernung eines Metasul-Inlays® beim Hüftpfannenwechsel", Operative Orthopädie und Traumaatologie 1998;10:157-8.
Effenberger, et al., "Röntgenkriterien und radiologische Ergebnisse der Hofer-Imhof(H-I)Schraubpfanne bei Erstimplantation", Z. Orthop. 135 (1997) 434-443.
Effenberger, et al., "X-ray criteria and radiological results of the Hofer-Imhof (H-I) threaded cup after primary implantation" English Version, J. Orthop. 135 (1997).
Delaunay, et al., "Acetabular Screw Rings and Surface Treatment", Clinical Orthopaedics and Related Research No. 340, pp. 130-141 1997.
Delaunay, et al., "Primary Total Hip Arthroplasty with the Karl Zweymüller First-generation Cementless Prosthesis", The Journal of Arthroplasty vol. 11 No. 6 1996.
Alpha Cera Fit, Various Prior Art Cups.
Product Feature, Orthopedic Product News, Oct. 1998.
Howmedica, "System 12® Acetabular Components" www.howmedica.com/products/frames/prod4-5.htm, Dec. 24, 1997.
Howmedica, "System 12™ Acetabular Components Designed to Address Issues of Acetabular Wear", Nov. 26, 1998.
Howmedica, "P.C.A.® total Hip system".
Howmedica, "System 12 Vitalock Cluster Acetabular Components", Oct. 1993.
Fuchs, "2-4 Year Clinical Results with a Ceramic-on-Ceramic Articulation in a New Modular THR-System", 5th Biolox Symposium 2000.
Fuchs, "2-4 Year Clinical Results with a Ceramic-on-Ceramic Articulation in a New Modular THR-System", 5th Biolox Symposium 2000 English Version.
Bohler, Results of metal-backed cup prostheses with ceramic inlay and a follow-up time of 4 years (implantation 1990) (12) (Fig. 3.2. 5a,b).
Furlong, "Six years use of the unmodified Furlong hydroxyapatite ceramic coated total hip replacement", Acta Orthop Belg 1993; 59 Suppl 1:323-325.
Lima-Lto, "SPH System, Acetabular Cups", Lima-Lto spa.
Furlong, et al., "Fixation of Hip Prostheses by Hydroxyapatite Ceramic Coatings", The Journal of Bone and Joint Surgery, 73(5):741-745, Sep. 1991.
Johnson & Johnson, "P.F.C.® BipolarHead", Johnson & Johnson Orthopaedics, 1994.
Johnson & Johnson, "Hip Systems", Johnson & Johnson Orthopaedics.
Johnson & Johnson, "Commitment Brochure", Johnson & Johnson Orthopaedics.
Johnson & Johnson, "UltimaJohnson & Johnson Orthopaedics,—Hüftsystem Schraubpfanne", Johnson & Johnson Orthopaedics.
Johnson & Johnson, "Das Ultima®—Hüftsystem", Johnson & Johnson Orthopaedics.
Wright Medical, "Interseal™ Acetabular Components Setting the Standard in Press-Fit Technology", Wright Medical Tecvhnology, Inc. 1994.
Osteonics, "The Osteonics® OCD Hip System, the Next Generation in Hip Fracture Management", Osteonics.
Dorlot et al., "Wear analysis of retrieved alumina heads and sockets of hip prostheses", J. Biomed. Mater. Res.: Applied Biomaterials, vol. 23, No. A3, 299-310 1989.
Ceraver S.C., "Technique De Mise En Place D'Un Cotyle Sans Ciment".
Dorlot, "Long-Term Effects of Alumina Components in Total Hip Prostheses", Clnical Orthopaedics 1991.

(56) References Cited

OTHER PUBLICATIONS

Dorlot, et al., "Examination of Retrieved Hip-Prostheses : Wear of Alumina/Alumina Components", Biological and Biomechanical Performance of Bimaterials, 1986.
Sedel, et al., "Aluminai-Alumina Hip Replacement in Patients Younger than 50 Years Old", Clinical Orthopaedics No. 298, pp. 175-183 1994.
Oberg, et al., "Machinery's Handbook Twentieth Edition", Industrial Press Inc., 1976.
"JRI Acetabular Cups", Joint Replacement Instrumentation Ltd.
Clarke, et al., "Development of a ceramic surface replacement for the hip. An experimental Sialong model", Biomater Med Devices Aartif Organs 1979; 7(1):111-126.
Lord, et al., "Cementless revisions of failed aseptic cemented and cementless total hip arthroplasties. 284 cases", Clnical Orthop Oct. 1988; 235:67-74.
Garcia-Cimbrelo, "Mittelmeier ceramic-ceramic prosthesis after 10 years", J Arthroplasty Oct. 1996; 11(7):773-781.
"Summary of Safety and Effectiveness Data" Feb. 3, 2003.
Intraplant, HI Cup Symposium "15 Jahre Jubiläum der HI-Pfanne", Intraplant AG, May 23, 2003.
Effenberger, et al., "Successful hip arthroplasty using cementless titanium implants in rheumatoid arthritis", Arch Orthop Trauma Surg (2002) 122: 80-87.
Ceraver Osteal, "Cerafit the cementless system", Ceraver Osteal.
Bizot, et al., "Alumina-on-Alumina Total Hip Prostheses in Patients 40 Years of Age or Younger", Clinical Orthopaedics and Related Research No. 379, pp. 68-76 2000.
Cerasiv, "The Ceramic Wear Couple Biolox in Total Hip Replacement", Program of Cerasiv's 1st International Symposium, Mar. 1996.
Park, et al., "Clinical Results of Sandwich type Ceramic-on-ceramic Couplings in Primary Cementless Total Hip Arthroplasty".
Effenberger, et al., "Criteria for Success with Trhreaded Cups (Design, Material and Modularity)", Acts Chirurgiae Orthopaedicae 70, 2003, p. 285-291.
Geesink, et al., "Six-Year Results of Hydroxyapatite-Coated Total Hip Replacement", The Journal of Bone and Joint Surgery, 1995.
Clarke, et al., "Role of ceramic implants. Design and clinical success with total hip prosthetic ceramic-to-ceramic bearings", Clinical Orthopaedics Sep. 1992; 282:19-30.
Boutin, et al., "The use of dense alumina-alumina ceramic combination in total hip replacement", Journal of Biomedical Materials Research, vol. 22, 1203-1232 1988.
Oberg, et al., "Machinery's Handbook—Standard Tapers", Industrial Press Inc., 1992.
"Industrial Belts and Sheaves", Gates 1988.
Aesculap, "Plasmacup®" Advertisement Brochure, The Journal of Bone and Joint Surgery, 1994.
Bläsius, et al., "CLS-Multicenter-Studie—8jährige Erfahrungen", Z. Orthop. 131 (1993).
Wölfel, et al., "Ergebnise nach zementloser Implantation von 150 Hüftprothesen „Erlanger Modell aus der Titanlegierung Ti A15 Fe2,5", Springer-Verlag 1993 96: 405-409.
Ahnfelt, "Prognosis of total hip replacement", Acta Orthop Scand 1990;61 (Suppl 238).
Furlong, "Prostheses and Instrumentation, the Furlong® H-A.C. Coated Total Hip Replacement Implants", Joint Replacement Instrumentation Ltd., Sep. 1985.
Christel, "Zirconia: The Second Genration of Ceramics for Total Hip Replacement", Bulletin of the Hospital for Joint Diseases Orthopaedic Institute 1989.
Allopro, "The Classic of Allo Pro", The Journal of Bone and Joint Surgery, Nov. 1996.
Averill, "Osteonics Technical Information Bulletin UHR® Performance in Circumstance of Postoperative Dislocation", Lit. No. OTB02-A—1986.
Osteonics, "The UHR® Universal Head Bipolar System Enhanced Fit, Performance and Security", The Science of Better Fit™, 1993.
"OTI Octeoimplant Technology, Inc.", Brochure.

Aldinger, "Individual-Hüftprothese CT3D-A", Orthopedic Services, Brochure.
Thümler, "CTX®-Das Fit System", Orthopedic Services, Brochure.
Ganz, "Pfannendachschale mit Haken", Ausgbe /195, deutsch, Protek.
Müller, "Self-Locking System SLS", Protek 1990.
Penta Medic, "Hip", Collection of Web Pages from http://www.pentamedical.com/Ehuefte.htm Seite 1 von 1, Jun. 8, 2002.
Link® FGK-Hüftpfannen, Waldemar Link GmbH & Co.
Bobyn, et al., "Interseal™ Acetabular Components Setting the Standard in Presss-Fit Technology", Wright Medical Technology 1995.
"Allilance™ Hip Systems, Biomet", Inc.
"Mallory-Head Hip Program Porous Revision Series", Biomet, Inc.
"Mallory-Head Hip Program Constrained Acetabular System", Biomet, Inc.
"Index™ Ringloc Acetabular Series", Biomet, Inc.
"Rothman Institute Hip Program, Taperloc Stem Universal Cup", Biomet, Inc.
"Mallory-Head Hip Program, Porous & Interlok Surgical Technique", Biomet, Inc. Oct. 31, 1994.
"RingLoc® Bi-Polar Articulating Hip System", Biomet, Inc.
"RingLoc® Acetabular Series, a Technical Report", Biomet, Inc.
"RingLoc® Acetabular Series", Biomet, Inc.
"The Products, www.ceraver.fr.anglais.PRODUITSang.htm", Ceraver.
"1970-1995 Our Osteolysis Challenge—A Successful Story with 25 Years Experience", Ceraver Osteal.
"Osteal Cerafit—Das Hybridsystem", Ceraver Osteal.
Osteal Product Data, Ceraver Osteal.
"The ANCA Fit System: truly designed to fit", Cremascoli Ortho Group.
Cremascoli Ortho Group Company Profile—www.orthoprodnews.co.uk/cop3.htm, International Orthopaedic Product News, Seite 1 von 3, Nov. 1, 1999.
"ANCA-Fit Surgical Technique", Cremascoli Ortho Group.
"Hüft-Endoprothetik Übersichi", DePuy.
"Product Feature", Orthopaedic Product News, p. 46, Oct. 1998.
"ESKA Genius® Hüft-System Cranial sockel", ESKA Implants AG.
"Eskaplan-System zur Erstellung originalgetreuer 3D-Modelle auf der Basis von CT-Daten", ESKA Implants GmbH & Co.
"ESKA-Hüft-Endoprothesen", ESKA Implants GmbH & Co.
"ESKA hip endoprosthetics" English version, ESKA Implants GmbH & Co.
"Product Feature", Orthopaedic Product News Oct. 1998, p. 42.
"Fehling Bivalent Modular Cup System—the answer to osteolysis", Fehling Memdical.
"Aesculap Orthopaedics—Endoprothesensysteme für Knie und Hüfte", Aesculap AG & Co.
"Aesculap Orthopaedics Plasmacup® zementfreies Hüftpfannensystem", Aesculap AG & Co.
"Aesculap Orthopaedics Plasmacup® delta zementfreie Pressfitpfanne mit Biolox® delta Einsätzen", Zesculap AG & Co.
"Alphanorm Product Brochure", Alphanorm.
"ABS Cup Alumina Bearing Surface, Ver. 2.0", Kyocera.
"Zementfreie Hüftprothesen Produkte-Information sterile Hüftgelenkpfanne", Mathys Orthopaedics 1993.
"Catalog Information on Synergy Instrumentation", Smith & Nephew 1999.
"Product Catalog", Stratec Medical Jan. 1997.
"UniTrax Unipolar System", Howmedica Jul. 1995.
Hedley, "Howmedica Surgical Techniques—The Vitalock® Acetabular Component System", Apr. 1996.
Smith & Nephew Richards, "Axis™ Hip System" Nov. 1996.
Dorn, et al., "The Metal-on-Metal Sliding Combination Concerning the HI Socket". Compendium of the Symposium on Apr. 25, 1998 in Salzburg, Prim. Univ. Doz. Dr. Ulrich Dorn.
Australian Patent Office, Patent Examination Report No. 2, dated Nov. 15, 2013, 4 pages.

\* cited by examiner

ACETABULAR CUP ASSEMBLY FOR MULTIPLE BEARING MATERIALS

CROSS-REFERENCE TO RELATED APPLICATIONS

This application is a National Stage of International Application No. PCT/US2006/06060044, filed Oct. 18, 2006, which claims the benefit of U.S. Provisional Application No. 60/783,937, filed Mar. 20, 2006. The disclosure of this application is incorporated by reference in its entirety.

BACKGROUND OF THE INVENTION

1. Field of the Invention

The present invention relates to acetabular cups and, more particularly, to acetabular cup assemblies for use with multiple bearings.

2. Related Art

In hip arthroplasty, various bearing materials are available for the acetabular cup portion of an implant. The selection of the bearing material is typically determined by the surgeon prior to performance of the procedure. At times, however, final selection of the bearing material is not completed until the implant site is prepared and conditions at the site are evaluated. Thus, it is sometimes advantageous to utilize an acetabular shell that accepts multiple bearing liners so that the surgeon can revise the initial assessment if required.

Acetabular shells that accept multiple bearings have been used in Europe since the early 1980s. Typically, the outer shell featured a tapered inside geometry in which a tapered hard or soft bearing could be inserted. In these cases, soft bearing thickness, lock integrity and wear performance were compromised in an effort to accommodate both bearings.

More recently, Stryker Corp. of Kalamazoo, Mich., U.S.A., has developed an acetabular cup that accepts a fully metal-encapsulated ceramic insert, which is held via a taper lock connection. The shell also accepts a polyethylene insert that is locked via one circumferential bead located mid-point along the inner taper and is rotationally stabilized by four conforming features between the shell and the liner.

An acetabular cup assembly for use with multiple bearings is desirable from a manufacturing standpoint because it is only necessary to produce one shell for use in many applications. This increases the volume of shells produced, which decreases overall production costs. Further, production of a single shell reduces distribution costs.

An acetabular cup assembly for use with multiple bearings is desirable from a revision standpoint because it gives the surgeon greater flexibility and reduces the overall time of the operation. First, the assembly gives the surgeon greater flexibility because the surgeon can easily make adjustments to the hip prosthesis. For example, if the original prosthesis had a polyethylene liner, the surgeon can easily substitute a ceramic or metal liner without changing the shell. Second, the assembly reduces the overall operation time because it is not necessary to remove the shell. Typically, the installed shell is surrounded by ingrown bone, which is very difficult and time consuming to remove. Further, removal of the installed shell may result in significant bone loss. By eliminating the step of removing the shell, the surgeon can complete the revision in less time with less effort and the result is less traumatic to the patient.

Micromotion between a polyethylene liner and an acetabular shell is undesirable as the motion creates polyethylene debris, which eventually causes bone osteolysis. Prior polyethylene bearing lock mechanisms were designed to exhibit minimal micromotion between the liner and the shell. However, these mechanisms also required an excessive interoperative insertion force for insertion of the liner. A high insertion force is undesirable as it requires greater effort on behalf of the surgeon to install the liner.

Traditionally, ceramic liner manufacturers have advised against reinsertion of ceramic liners due to the stress-sensitive nature of the material. The material may fracture or break if stressed inappropriately. However, for various reasons, it may be desirable to remove and reinstall a liner. As an example, a surgeon may want to remove the ceramic liner during installation, change the shell position, and reinstall the liner. As ceramic manufactures presently advise against this, a surgeon takes on great risk when making these types of adjustments during ceramic liner installations.

There remains a need in the art for an acetabular cup assembly for use with multiple bearings.

SUMMARY OF THE INVENTION

The invention is, briefly, an acetabular cup assembly. The assembly includes a shell and a liner. The shell has an inner surface and an outer surface. The inner surface has a first groove, a second groove, and a tapered inner wall. The liner is adapted to fit within the inner surface of the shell. The liner is selected from the group consisting of a polymer liner, a ceramic liner, and a metal liner, and the polymer liner has an inner portion and an outer portion, the outer portion includes a first bump and a second bump, the ceramic liner includes a band, and the metal liner includes a tapered outer portion.

In one embodiment of the invention, the polymer liner is selected from the group consisting of cross-linked polyethylene and conventional polyethylene.

In another embodiment of the invention, the liner includes anti-rotation tabs and the shell includes at least one scallop. The scallops are dimensioned to receive the anti-rotation tabs.

In yet another embodiment of the invention, the shell includes an insertion tool hole. The insertion tool hole may be used in conjunction with a tool to install the shell.

In still another embodiment of the invention, the inner surface of the shell is highly polished. The inner surface may have a surface roughness of about one to about sixteen microinches, and rather about one to about eight microinches. The highly polished surface reduces polymer liner debris if micromotion happens to occur between the shell and the liner.

In another embodiment of the invention, the shell is made from a material selected from the group consisting of titanium, cobalt chromium, and stainless steel.

In yet another embodiment of the invention, the shell further comprises at least one fixation hole. The fixation hole is adapted to receive one or more fixation devices to attach the shell to bone.

In still another embodiment of the invention, the shell further comprises a porous coating on the outer surface. The porous coating allows for bone in-growth.

In another embodiment of the invention, the band has a taper. The band may be tapered from about two degrees to about thirty-six degrees, and rather the band has a taper of about eighteen degrees.

In yet another embodiment of the invention, the tapered inner wall, the band or the tapered outer portion includes a surface enhancement. The surface enhancement may be selected from the group consisting of an acme-type stair-step, a reverse stair-step, or a predetermined surface roughness. The surface enhancement augments the locking of the liner.

In still another embodiment of the invention, the acetabular cup assembly may have a constrained bearing liner. The liner may utilize a locking feature, such as a metal locking ring or an annular flange.

The acetabular cup assembly may have a two-piece liner that includes a bearing surface component and a capture mechanism. The capture mechanism is locked into the shell after hip reduction.

In another embodiment of the invention, the liner is selected from the group consisting of a constrained liner, a neutral liner, an anteverted liner, a lipped bearing liner, and a lateralized bearing liner.

In yet another embodiment of the invention, the acetabular cup assembly further comprising an installation tool attached to the liner. The installation tool is comprised of metal or plastic.

In one particular embodiment of the invention, the invention is a modular acetabular cup assembly for use with multiple bearing liners. The acetabular cup assembly includes a shell having an inner wall, two annular grooves, and a plurality of anti-rotation tabs. The shell may be used with polyethylene, ceramic, metal, and other types of liners. In the case of a ceramic liner, a band is attached to the liner. The band is adapted to mate with the inner wall. The band on the ceramic liner enables the shell to be used with an off-the-shelf liner without the need for more expensive, custom made liners.

In yet another embodiment of the invention, the shell has a face and an apex, a central axis extends through the apex, a line extends from where the inner surface meets the lower groove to where the central axis meets a planar surface defined by a plane extending through the face of the shell, the central axis and the line defining an angle, and wherein the angle ranges from about ten degrees to about eighty degrees. In other embodiments, the angle ranges from about forty to about seventy degrees.

In another embodiment of the invention, the first groove and the second groove are separated by a first distance, and the first distance ranges from about one millimeter to about twenty millimeters. In other embodiments, the first distance ranges from about two millimeters to about four millimeters.

In yet another embodiment of the invention, the band has an inner surface and an outer surface spaced apart from the inner surface by a second distance, and the second distance varies from about one-half millimeter to about 30 millimeters. In other embodiments, the distance ranges from about one-half millimeter to about ten millimeters.

The invention offers the advantage of two annular grooves or cavities that receive annular bumps or ribs of the liner. The grooves may or may not fully extend about an interior of the shell. The use of two ribs and grooves is significant as the effective push-in and push-out of the liner can be controlled and optimized by adjusting the tolerances and dimensions of these four items and the interference between the shell and the liner. Thus, the acetabular cup assembly may be designed such that a surgeon may easily be able to push-in the liner by hand but the liner will not disassemble from the shell without the use of a tool.

The band also allows the ceramic liner to be reinserted should this become necessary interoperatively. Furthermore, the band improves the force distribution around the liner and significantly reduces the potential for liner fracture, particularly in the event of a misalignment.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE EMBODIMENTS

The following description of the preferred embodiments) is merely exemplary in nature and is in no way intended to limit the invention, its application, or uses.

Figure 1:
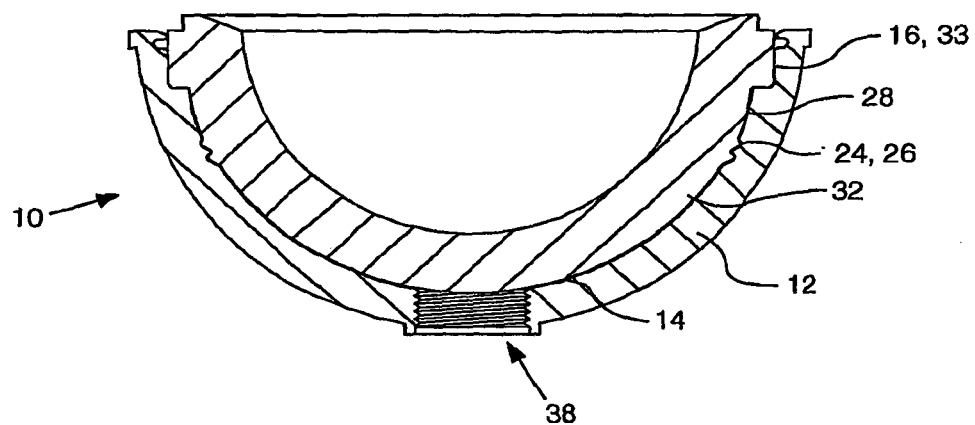
FIG. 1 is a sectional side view of an acetabular cup assembly in a first embodiment.
Figure 2:
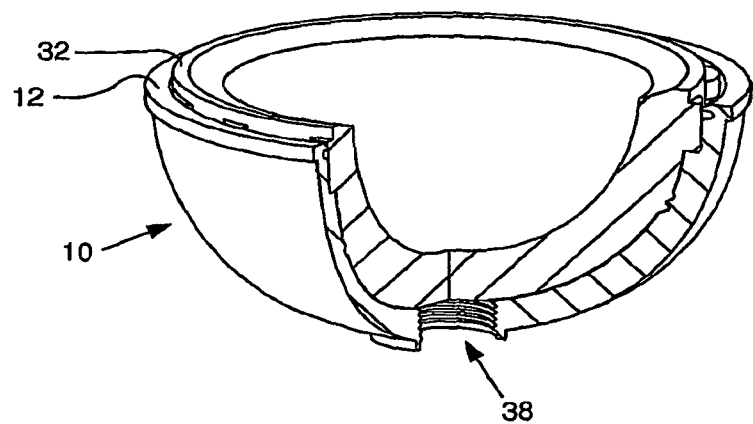
FIG. 2 is a front perspective view of the acetabular cup assembly shown in FIG. 1.

FIGS. 1 and 2 illustrate an acetabular cup assembly 10. The acetabular cup assembly 10 includes a shell 12. The shell 12 is adapted for use with multiple bearing liners, such as a first liner 32. The first liner 32 may be any number of liners but is a polymer liner in the embodiment depicted in FIGS. 1 and 2. For example, the first liner 32 may be a cross-linked polyethylene liner or a conventional polyethylene liner. The first liner 32 includes anti-rotation tabs 33. The shell 12 includes an insertion tool hole 38, which is used to receive a tool (not shown) for installation of the shell. In the depicted embodiment, the insertion tool hole 38 is threaded.

Figure 3:
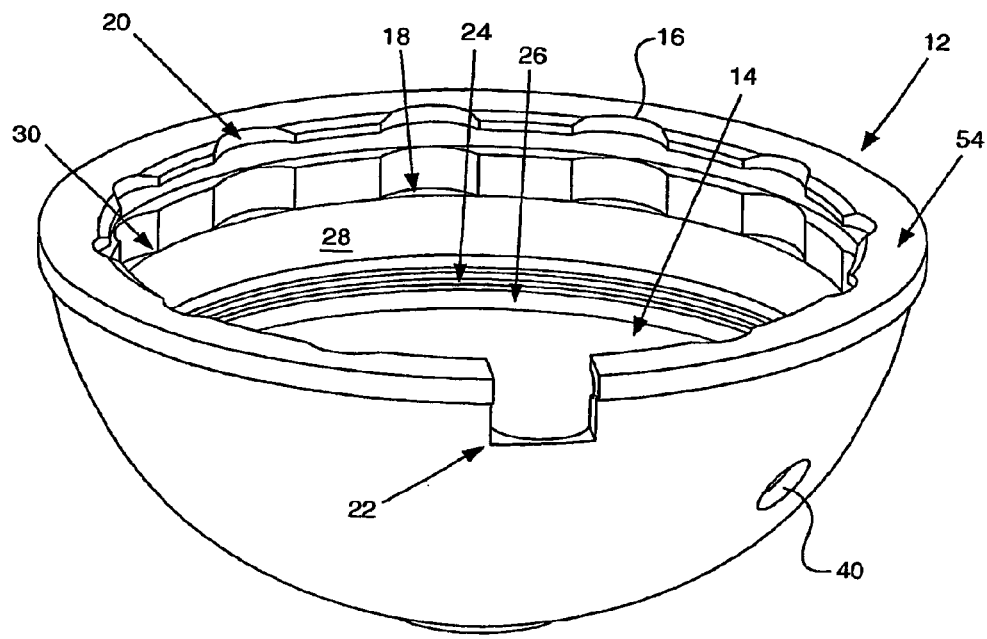
FIG. 3 is a front perspective view of a shell.

As best seen in FIG. 3, the shell 12 includes an inner surface 14. In the embodiment illustrated in FIG. 3, the inner surface 14 has a concave shape but other shapes may be used In some embodiments, the inner surface 14 is highly polished such that it appears mirror-like. For example, the inner surface may have a roughness from about one microinch to about sixteen microinches. In the depicted embodiment, the inner surface has a roughness from about eight microinches to about sixteen microinches. In some embodiments, the inner surface has a roughness of about 1 microinch to about eight microinches. A highly polished inner surface 14 significantly reduces or prevents polymer liner debris generation.

In the embodiment depicted in FIG. 3, the shell 12 is made of metal but those skilled in the art would understand that other materials could equally be used. As examples, the shell 12 may be made of titanium, cobalt chromium, stainless steel, or other biocompatible material.

The shell 12 includes a face 54 and scallops 16 which receive anti-rotation tabs 33. In the embodiment depicted in FIG. 3, the shell 12 includes twelve scallops 16 and the first liner 32 has twelve corresponding anti-rotation tabs 33 to achieve greater microstability. Each scallop 16 forms a lip or ledge 18 on an inner wall 28 of the shell 12. The shell 12 further includes an annular groove 20 that extends peripherally or circumferentially about the inner wall 28. The shell 12 also includes a notch 22. The notch 22 allows a pry tool access to the liner portion of the assembly.

In some embodiments, the shell 12 may include one or more fixation holes 40. A screw, modular peg, or other fixation device (not shown) may be inserted through the fixation hole 40 to attach the shell 12 to bone. Further, in some embodiments the shell may have a porous coating on its exterior. As examples, the exterior of the shell 12 may have a sintered metal coating, a vapor deposited metal coating, a thermal spray metal coating, or be chemically etched. The porous coating may allow for bone in-growth into the shell 12.

Figure 4:
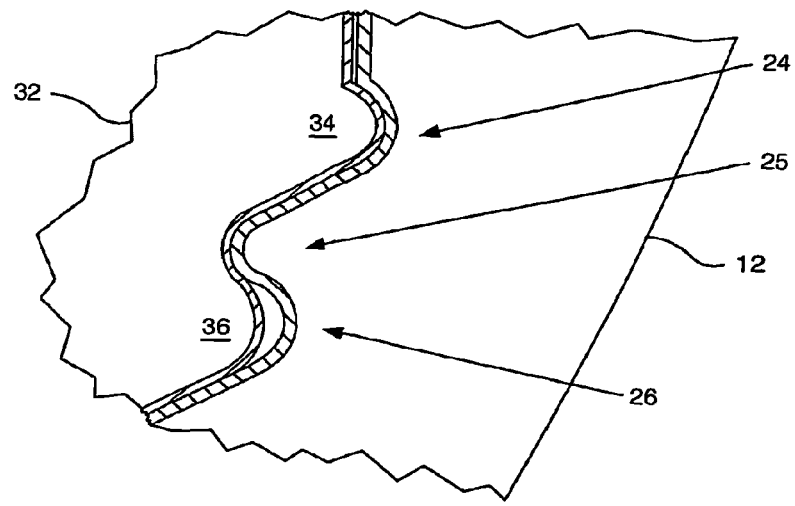
FIG. 4 is a partial sectional side view of the acetabular cup assembly.

The inner surface 14 forms a first groove 24 and a second groove 26. Alternatively, the grooves 24, 26 may be termed indentations or cavities. The grooves 24, 26 may or may not fully extend about an interior 30 of the shell 12. Thus, the grooves 24, 26 may form annular rings, have a "C" shape, be intermittently spaced about the circumference, have a hemispherical shape, or have some other shape. As best seen in FIG. 4, the first groove 24 and the second groove 26 respectively receive a first bump 34 and a second bump 36 of the first liner 32. The first bump 34 alternatively may be referred to as a first insertion member or first rib, and the second bump 36 alternatively may be referred to as a second insertion member or second rib. In the case of a metal or ceramic liner, the bumps 34, 36 may be a separate component, such as a split ring or spring, or molded to the exterior of the liner.

The use of two protrusions and grooves is significant as the effective push-in and push-out of the liner 32 can be controlled by adjusting the tolerances and dimensions of these four items. For example, it is possible to have the liner 32 installed with a small push-in force but also have a significant push-out force. Thus, a surgeon may easily be able to push-in the liner by hand but the liner will not disassemble from the shell without the use of a tool. In another example, the liner 32 may be installed with a high push-in force and have an even greater push-out force. A protrusion 25 is formed as part of the inner surface 14 in between the grooves 24, 26. By controlling the interference between the protrusion 25 and the second bump 36 and the other dimensions, one can adjust the push-in and push-out force. If the second bump 36 greatly interferes with the protrusion 25, then the liner 32 will have both a high push-in and push-out. In this case, it may be necessary to significantly cool the liner 32 prior to installation to temporarily reduce its size. However, if the second bump 36 only slightly interferes with the protrusion 25, then the liner 32 may be inserted utilizing a low push-in force and removed utilizing a high push-out force. This is because once the bumps 34, 36 engage the grooves 24, 26, both bumps will contribute to the push-out force required. However, in the case of push-in, the force required is only enough for the second bump 36 to clear the protrusion 25 and for the first bump 34 to engage the first groove 24.

The first groove 24 and the second groove 26 are located below the inner wall 28. This is significant because the location of the grooves 24, 26 shelters the locking mechanism of the first liner 32 from soft tissue interference. In other words, because the bumps 34, 36 engage the grooves 24, 26 on a lower portion of the shell 12, the likelihood of soft tissue interference with the locking of the first liner 32 to the shell is significantly reduced.

Figure 5:
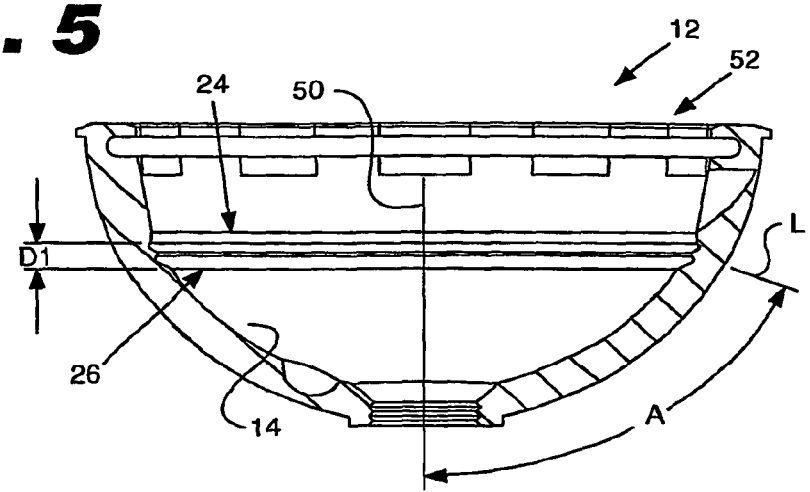
FIG. 5 is a sectional side view of the shell.

FIG. 5 illustrates a section side view of the shell 12. The shell 12 has a central axis 50 that extends through the apex of the shell. The grooves 24, 26 are located on the inner surface 14 of the shell 12. A line L extends from where the inner surface 14 meets the lower groove 26 to where the central axis 50 meets a planar surface 52. The planar surface 52 is defined by a plane extending through the face 54 of the shell 12. An angle A is defined by the central axis and the line L. The angle A is about 10 degrees to about 80 degrees. In the embodiment depicted in FIG. 5, the angle A is about 40 degrees to about 70 degrees. FIG. 5 also illustrates a first distance or dimension D1. The dimension D1 is the distance between the upper groove 24 and the lower groove 26. The dimension D1 is about 1 to about 20 millimeters. In the embodiment depicted in FIG. 5, the dimension D1 is about 2 to about 4 millimeters.

Figure 6:
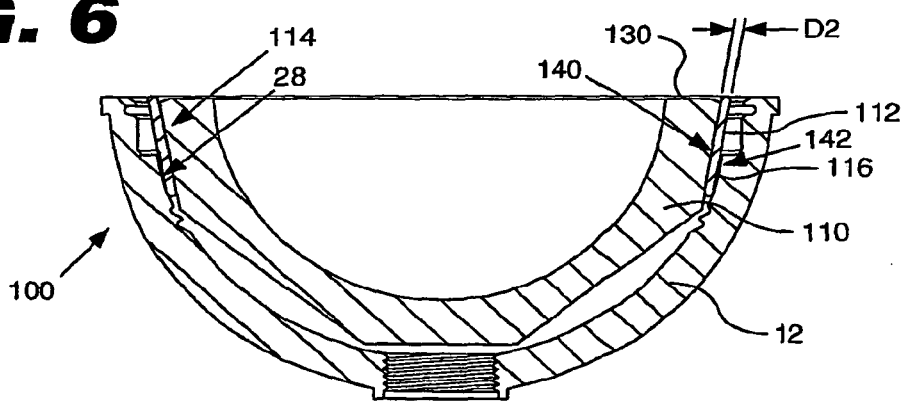
FIG. 6 is a sectional side view of an acetabular cup assembly in a second embodiment.
Figure 7:
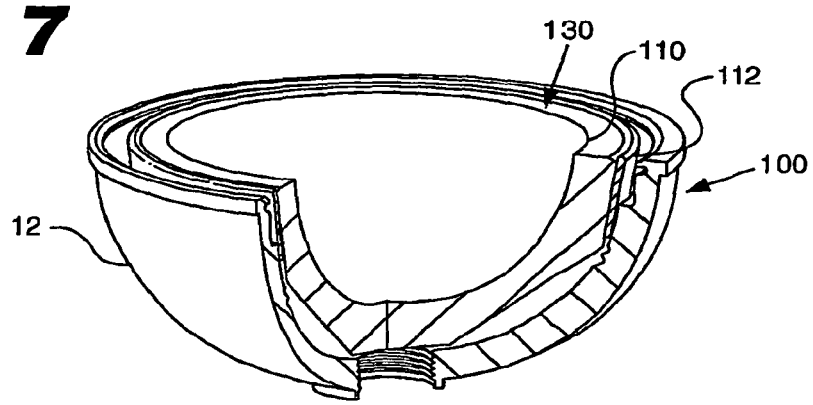
FIG. 7 is a partial front perspective view of the acetabular cup assembly shown in FIG. 6.

FIGS. 6 and 7 illustrate a second embodiment of the acetabular cup assembly, generally indicated by reference numeral 100. The acetabular cup assembly 100 includes a second liner 110, a band or ring 112, and the shell 12. As an example, the second liner 110 may be a ceramic liner, such as an alumina ceramic liner. Further examples include a diamond liner, a liner made of a polycrystalline diamond composite material, a liner made from oxidized Zirconium, or a liner made from polyethylene, including cross linked polyethylene. The band 112 may be made of metal. For example, the band 112 may be made of stainless steel, titanium, cobalt chromium, or a shape memory alloy, such as nitinol. The band 112 is affixed to an outer portion 114 of the liner 110. The band 112 is adapted to mate with the inner wall 28 of the shell 12. The band 112 and the inner wall 28 may be tapered. For example, the inner wall 28 may be tapered from about two degrees to about thirty-six degrees. In the embodiment depicted in FIG. 6, the inner wall 28 has about an eighteen degree taper. The band 112 allows a ceramic liner to be removed and reinserted. This is significant, as previously removal and reinstallation of a ceramic liner was inadvisable. Further, the band 112 improves the force distribution around the second liner 110 and eliminates, or at least significantly reduces, the potential for cracking of a ceramic liner upon insertion, especially if there is any misalignment. The liner 110 has a face 130. The band 112 may extend above the face 130, below the face 130, or substantially flush with the face 130. If the band 112 extends above the face 130, the band 112 may prevent impingement in some circumstances. In the embodiment depicted in FIGS. 6 and 7, the band is substantially flush with the face 130.

The band 112 has an inner surface 140 and an outer surface 142 spaced apart from the inner surface 140. The inner surface 140 is sized and shaped to complement the outer portion 114 of the liner 110, and the outer surface 142 is sized and shaped to complement the inner wall 28. The outer surface 142 is spaced apart from the inner surface 140 by a second distance or second dimension D2. The distance D2 may vary from about one-half millimeter to about 30 millimeters, and rather from about one-half millimeter to about ten millimeters. In the embodiment depicted in FIG. 6, the distance D2 is about three-fourths of a millimeter.

In some embodiments, the shell 12 may accept differently sized liners. The acetabular cup assembly 100 may include a plurality of liners, each having a band with a differently sized inner surface but each having the same size outer surface. Thus, the plurality of liners all fit the same shell because the outer surface is the same size. However, the inner surface is differently sized allowing for differently sized liners. The difference in size is adjusted by adjusting the distance D2 of the band 112. As an example only, the single shell 12 may accept 26, 28, and 32 millimeter inner diameter liners. This is significant as the modularity reduces manufacturing costs and provides surgeons with a greater number of intraoperative choices.

In other embodiments, the liner 110 may fit within differently sized shells. The acetabular cup assembly 100 may include a plurality of liners, each having a band with a differently sized outer surface but each having the same size inner surface. Thus, the plurality of liners each have the same inner diameter size but has differently sized outer surface that complements a particular size of shell. The difference in size is adjusted by adjusting the distance D2 of the band 112. As an example only, the single liner 110 may fit within 46, 48, and 50 millimeter inner diameter shells. This is significant as the modularity reduces manufacturing costs and provides surgeons with a greater number of intraoperative choices.

Figure 8:
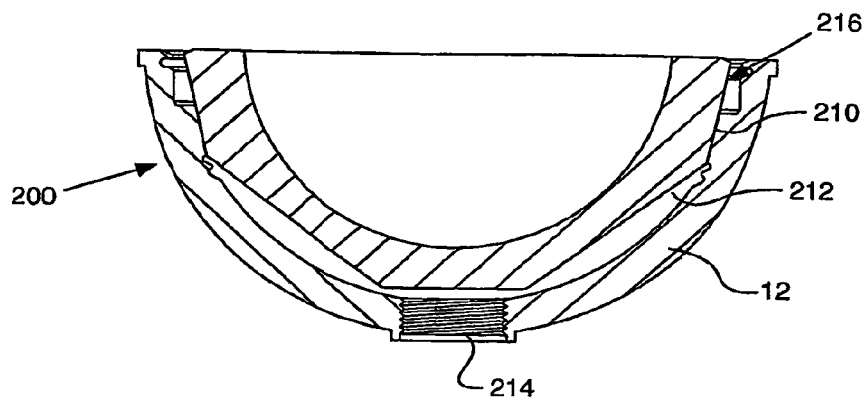
FIG. 8 is a sectional side view of an acetabular cup assembly in a third embodiment.
Figure 9:
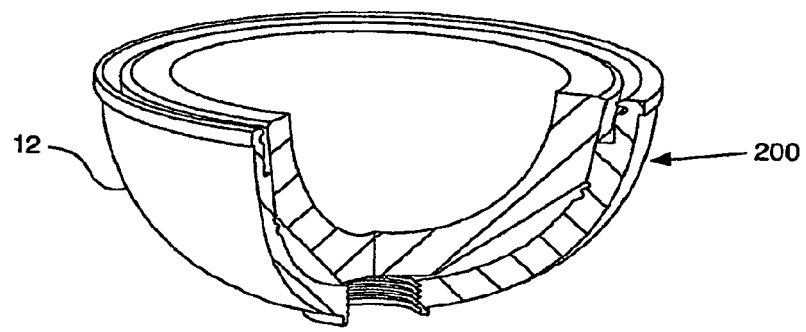
FIG. 9 is a partial front perspective view of the acetabular cup assembly shown in FIG. 8.

FIGS. 8 and 9 illustrate a third embodiment of the acetabular cup assembly, generally indicated by reference numeral 200. The acetabular cup assembly 200 includes a third liner 212 and the shell 12. As an example, the third liner 212 may be a metal liner, such as cobalt chromium. Alternatively, the third liner 212 may be a ceramic, plastic, or composite. The liner 212 includes an outer portion 216. The outer portion 216 is adapted to mate with the inner wall 28 of the shell 12. The outer portion 216 and the inner wall 28 may be tapered. For example, the inner wall 28 may be tapered from about two degrees to about thirty-six degrees. In the embodiment depicted in FIG. 8, the inner wall 28 has about an eighteen degree taper. In some embodiments, the assembly 200 may further include plug 214. The plug 214 may be used to cover fixation devices or used to fill unused holes. In FIG. 9, the plug 214 has been removed for clarity.

Figure 10:
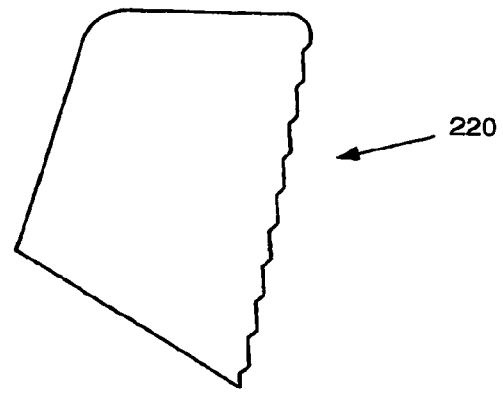
FIG. 10 is a first embodiment of a surface enhancement.
Figure 11:
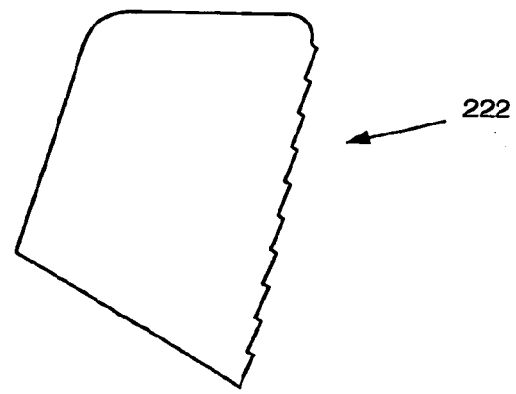
FIG. 11 is a second embodiment of a surface enhancement.
Figure 12:
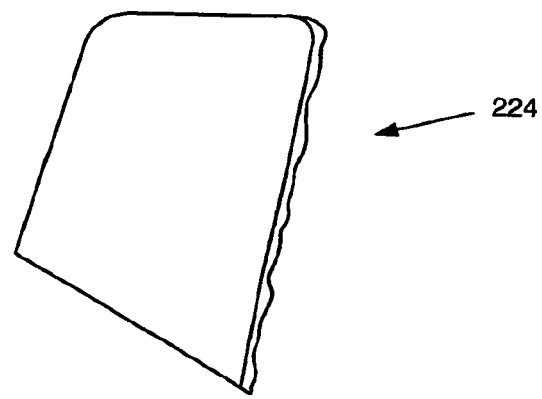
FIG. 12 is a third embodiment of a surface enhancement.

FIGS. 10, 11, and 12 illustrate various surface enhancements that may be applied to the band 112 or the outer portion 214 for lock enhancement of the liner. In FIG. 10, an Acme-type "stair-step" 220 may be machined into the band 112 or the outer portion 216. Similarly, in FIG. 11 a "reverse stair-step" 222 may be machined into the band 112 or the outer portion 216. The stair-step surface configuration 220 or the reverse stair-step configuration may be used to maintain lock integrity even after multiple reinsertions. In FIG. 12, the band 112 or the outer portion 216 may have predetermined surface roughness 224. The surface roughness 224 may be achieved by coarse media blasting, such as by grit blast, glass bead blast, etc. Alternatively, the surface enhancements 220, 222, 224 could be applied to the inner wall 28. Moreover, numerous types of coatings may be applied to the band 112, the outer portion 214, or the inner wall 28. As examples, these surfaces may have a metal, plastic, diamond, or composite coating.

Figure 13:
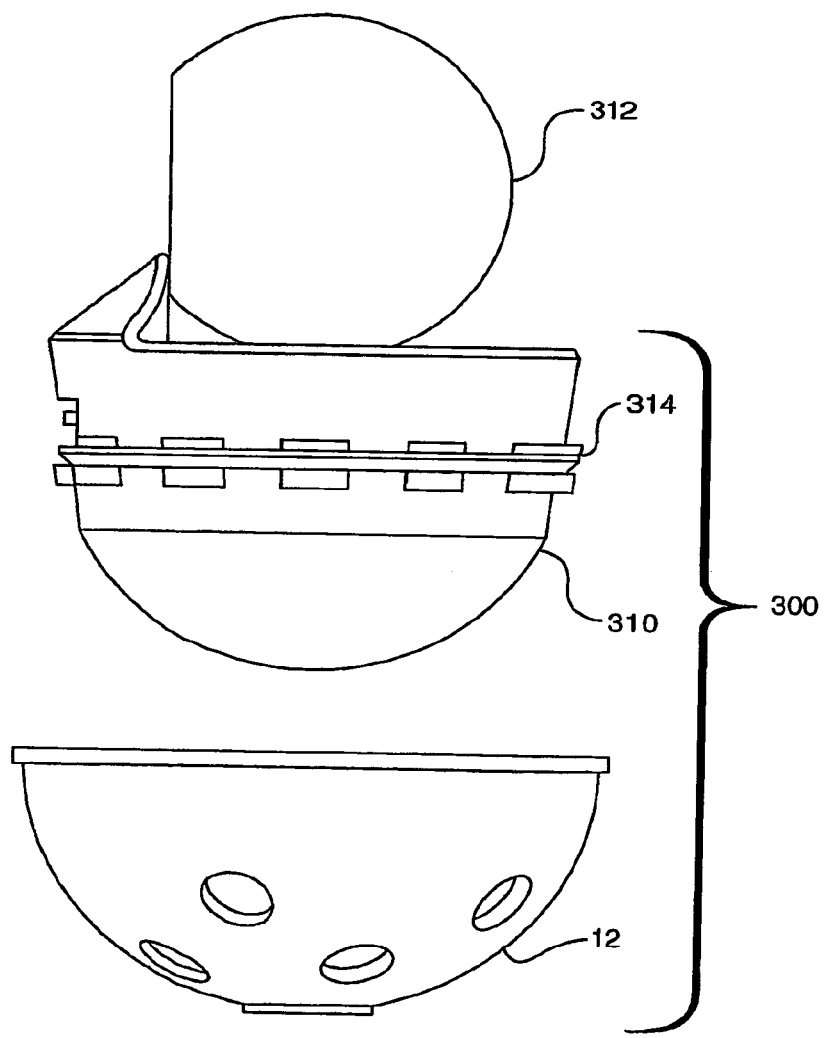
FIG. 13 is an exploded side view of an acetabular cup assembly in a fourth embodiment.

FIG. 13 illustrates a fourth embodiment of the acetabular cup assembly, generally indicated by reference numeral 300. The acetabular cup assembly 300 includes the shell 12 and a constrained bearing liner 310. In a constrained bearing liner, a femoral head 312 is captured within the liner. Constrained bearing liners often utilize a third locking feature as they typically require a higher disassociation force. In FIG. 13, a metal locking ring 314 interfaces with the first groove 24. Alternatively, an annular flange may be attached to the liner and the annular flange engages the first groove 24. The locking ring 314 may be used with either a one-piece or two-piece constrained liner construct.

Figure 14:
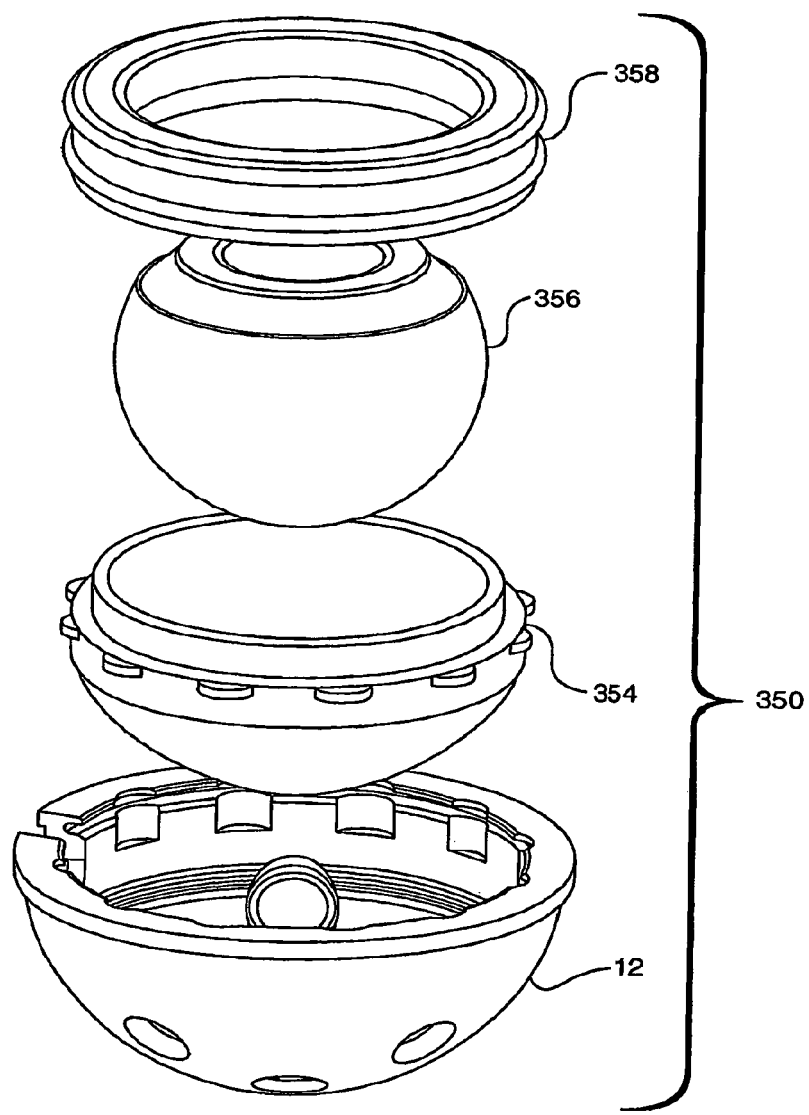
FIG. 14 is an exploded side view of an acetabular cup assembly in a fifth embodiment.

FIG. 14 illustrates a fourth embodiment of the acetabular cup assembly, generally indicated by reference numeral 350. The acetabular cup assembly is a two-piece construct that includes the shell 12, a bearing surface component 354, and a capture mechanism 358. For the two-piece construct, the bearing surface component 354 is inserted into the shell, the femoral head 356 is placed in the liner, and the capture mechanism 358 is placed over the femoral component 356 prior to head assembly. Once the hip is reduced, the capture mechanism 358 is inserted and locked into the shell, thereby securing the full assembly construct. As an example, the capture mechanism may engage the annular groove 20 (best seen in FIG. 3).

The liners 32, 110, 212, 310, 354 may be neutral liners, anteveretd bearing liners, lipped bearing liners, or lateralized bearing liners. Thus, the depicted embodiments are merely exemplary. Further, an interior or an exterior of the liners 32, 110, 212, 310, 354 may be coated with various types of coatings. For example, these surfaces may have a metal, plastic, diamond, or composite coating.

Figure 15:
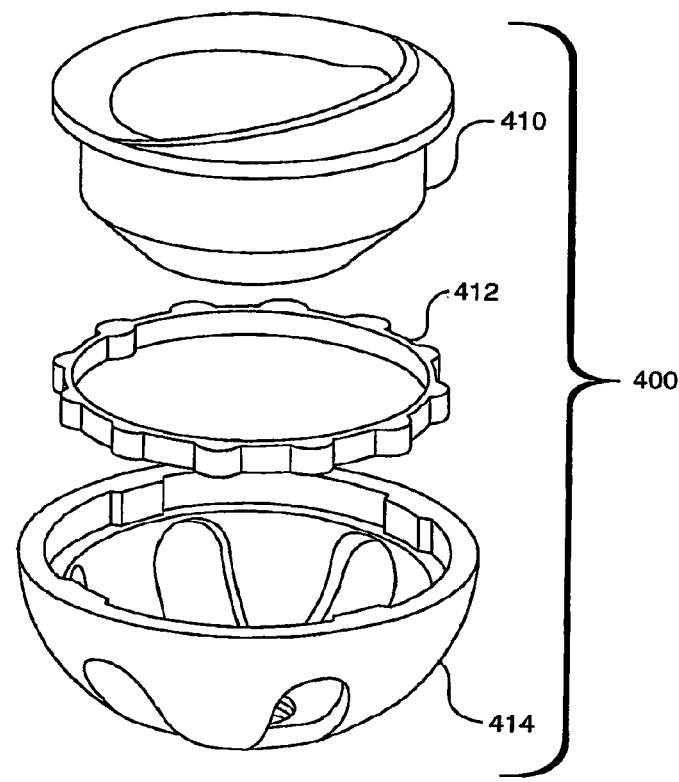
FIG. 15 is an exploded front perspective view of a modular acetabular trialing system.
Figure 16:
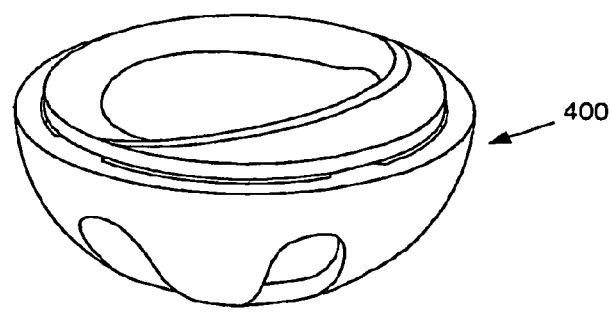
FIG. 16 is a front perspective view of the modular acetabular trialing system shown in FIG. 15.
Figure 17:
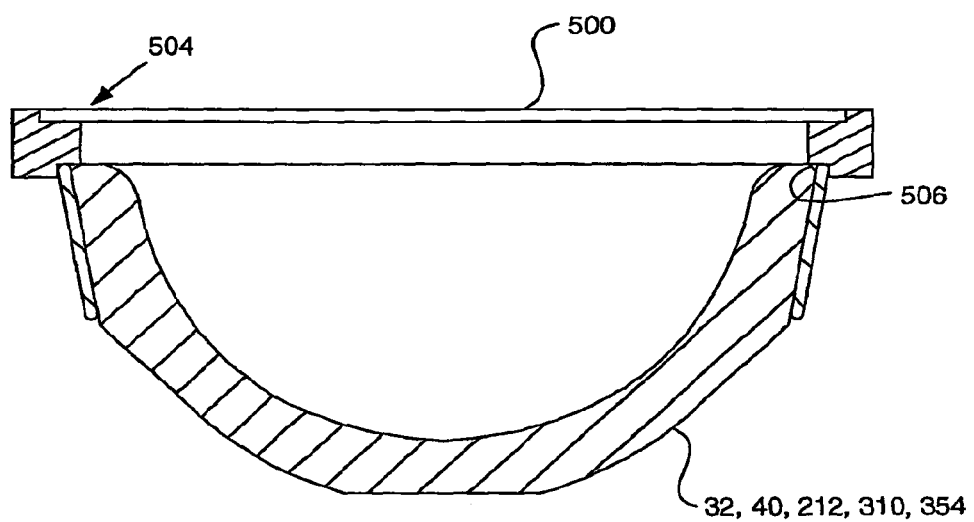
FIG. 17 is a sectional side view of an installation tool in a first embodiment in use on a liner.
Figure 18:
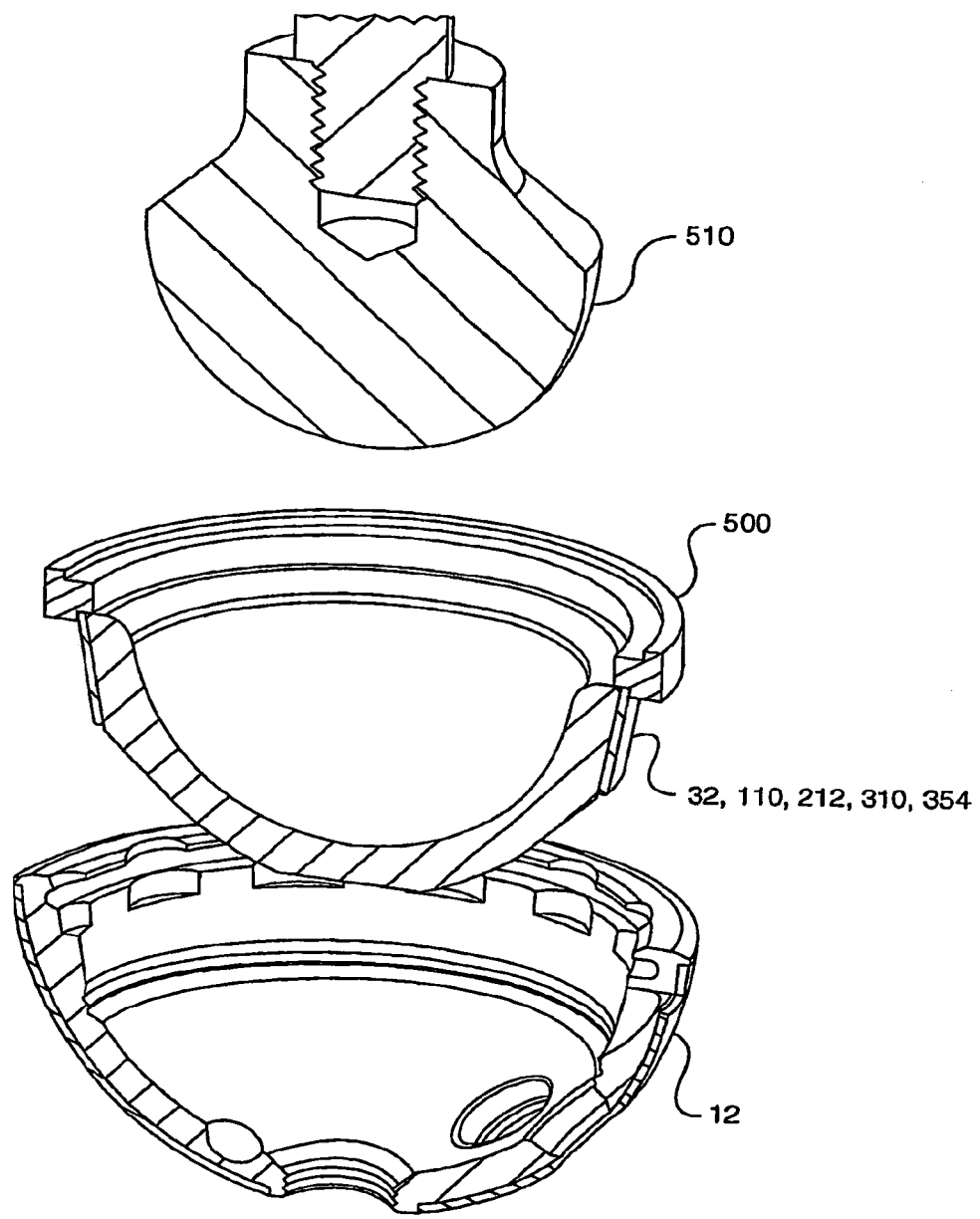
FIG. 18 is a front perspective exploded sectional view of the shell, the installation tool applied to the liner, and an impactor head.
Figure 19:
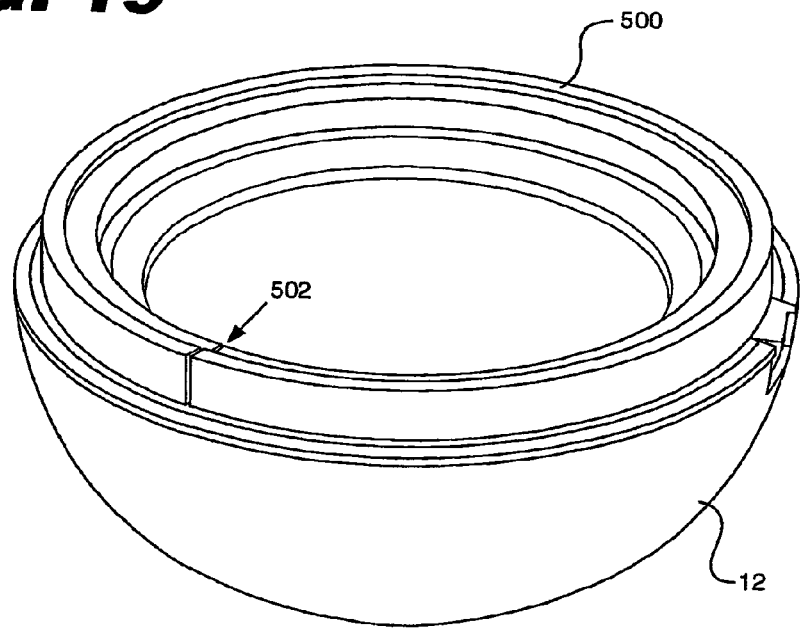
FIG. 19 is a front perspective view of the shell, installation tool, and liner.
Figure 20:
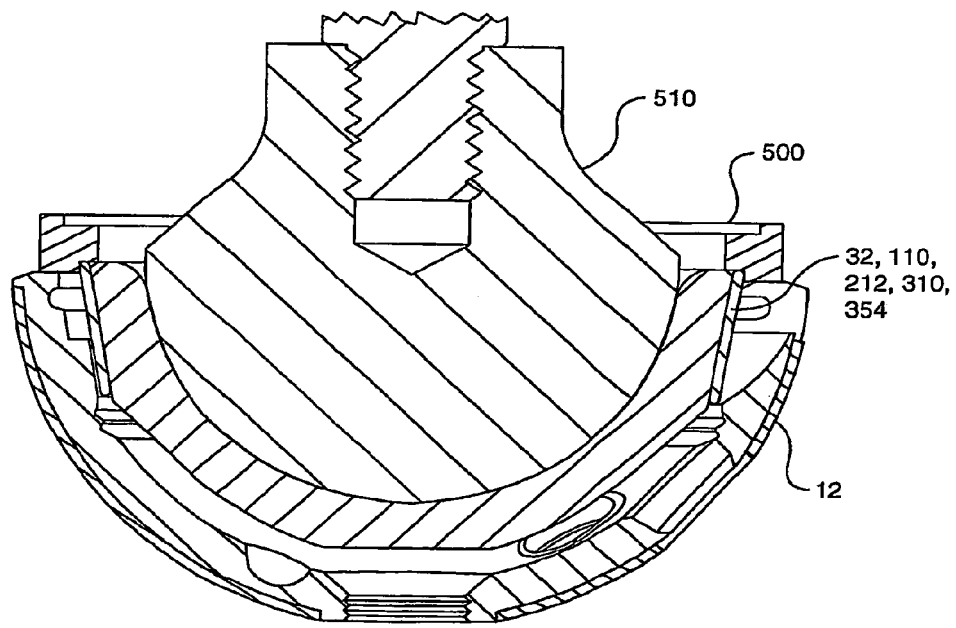
FIG. 20 is a sectional side view of the shell, the installation tool applied to the liner, and the impactor head.

FIGS. 15 and 16 illustrate a modular acetabular trialing system 400. The acetabular trialing system 400 includes a trial liner 410, a trial spacer 412, and a trial shell 414. Modularity greatly reduces the number of trialing components necessary to cover the full range of sizes offered in the acetabular cup system, which further simplifies the amount of instrumentation required for surgery. The trial liner 410 and the trial spacer 412 may be used with the trial shell 414 or the implantable shell 12.

FIGS. 17, 18, 19 and 20 illustrate a method and apparatus for installing the liner 32, 110, 212, 310, 354. A first embodiment of an installation tool 500 is attached to the liner 32, 110, 212, 310, 354. The installation tool 500 is substantially circular. In some embodiments, the installation tool 500 has a cutout 502. The installation tool 500 has a first shoulder 504 and a second shoulder 506. Alternatively, these features may be termed as a first capture recess 504 and a second capture recess 506. In some embodiments, the first shoulder is identical to the second shoulder such that either side of the installation tool may be used. In other embodiments, the first shoulder 504 is larger or smaller than the second shoulder 506 such that the installation tool 500 may accommodate various sizes of liners 32, 110, 212, 310, 354. The first shoulder 504 and the second shoulder 506 may be square or tapered. In the tapered embodiments, the first and second shoulders 504, 506 may taper outwardly for manufacturing purposes or taper inwardly to provide line contact with the liner.

In the method, the installation tool 500 is slightly spread open and attached to the liner 32, 110, 212, 310, 354 until either the first shoulder 504 or the second shoulder 506 contact the liner. The installation tool 500 is resilient and biased to spring back into its original position. Thus, the installation tool 500 is attached to the liner 32, 110, 212, 310, 354 through the use of a spring force.

Once the installation tool 500 is assembled to the liner 32, 110, 212, 310, 354, the installation tool 500 and the liner 32, 110, 212, 310, 354 are placed over the shell 12. Thereafter, an impactor head 510 may be used to press on the liner 32, 110, 212, 310, 354 to remove the liner from the installation tool 500 and install the liner in the shell 12. The use of the installation tool 500 allows for automatic centering and alignment of the liner 32, 110, 212, 310, 354 within the shell 12. The use of the installation tool 500 significantly reduces the possibility that the liner may become askew relative to the shell upon installation. Further, the installation tool 500 may serve as a soft tissue retractor during installation. The outer portion of the installation tool 500 may be used to push soft tissue aside as the liner is inserted into the shell.

The installation tool 500 may be re-usable or disposable. For example, the installation tool 500 may be made of metal, such as stainless steel, and the installation tool may be sterilized and re-used after installation of the liner. Alternatively, the installation tool 500 may be made from a polymer or plastic and disposed of after liner insertion. In the case of a plastic material, the installation tool may be color coded to indicate a particular size or to indicate a particular brand.

Figure 21:
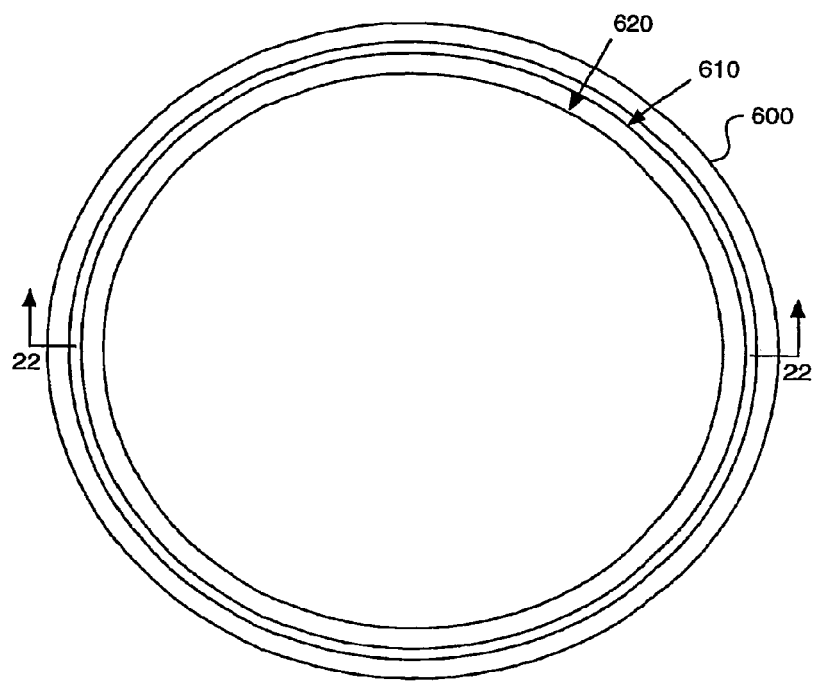
FIG. 21 is a top view of the installation tool in a second embodiment.
Figure 22:
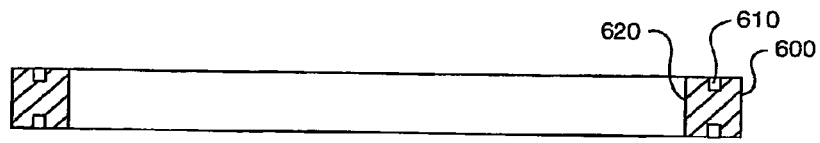
FIG. 22 is a sectional front view of the embodiment shown in FIG. 21.

FIGS. 21 and 22 illustrate a second embodiment of the installation tool, generally indicated by numeral reference 600. The installation tool 600 includes a notch 610. The notch 610 allows an inner portion 620 of the installation tool 600 to flex. Thus, the bending of the inner portion 620 provides a spring force that can be applied to the liner 32, 110, 212, 310, 354. Similar to the first embodiment, the installation tool 600 is assembled to the liner 32, 110, 212, 310, 354, the installation tool 600 and the liner are placed over the shell 12. Thereafter, an impactor head 510 may be used to press on the liner to remove the liner from the installation tool 600 and install the liner in the shell 12. The use of the installation tool 600 allows for automatic centering and alignment of the liner within the shell 12.

Figure 23:
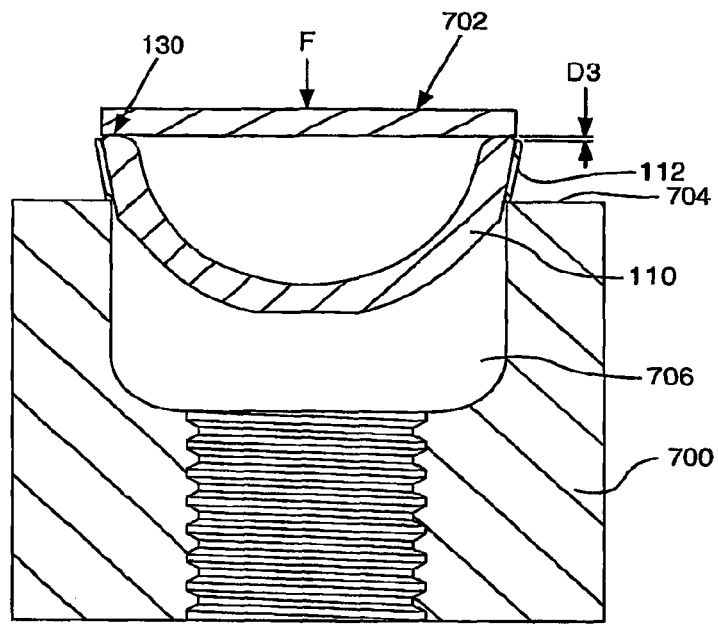
FIG. 23 is a sectional front view of a fixture for mounting a band to a liner in a first embodiment.

FIG. 23 illustrates a first embodiment of a fixture 700 for use in installing the band 112 on the liner 110. The fixture 700 includes a fixture face 704 and a well 706. To install the band 112 on the liner 110, the band 112 and the liner 110 are placed on the fixture 700 and a press (not shown) with a press platen 702 is used to press the band 112 on the liner 110. First, the fixture 700 is mounted to the press, which may be a computer numerically controlled press. Second, the press is set with a displacement rate, a minimum force, and a maximum force. The displacement rate may be from about 0.01 inch per minute to about 2.00 inches per minute maximum. In the depicted embodiment, the displacement rate is about 0.80 inches per minute to about 1.10 inches per minute maximum. The minimum force ranges from about 5000 pounds to 11000 pounds. In the depicted embodiment, the minimum force is about 8000 pounds. The maximum force ranges from about 8000 pounds to about 15000 pounds. In the depicted embodiment, the maximum force is about 10000 pounds. Third, the band 112 is placed on the liner 110 by hand. Fourth, the band 112 and the liner 110 are placed on the fixture 700 with the liner 110 protruding into the well 706 and the band 112 resting on the fixture face 704. Fifth, the press platen 702 is advanced until it makes contact with the face 130 of the liner 110. The initial preload force on the liner 110 may be from about zero pounds to about ten pounds. Sixth, the press platen 702 applies a force F on the liner 110 until a displacement D3 is achieved between the band 112 and the liner 110. The displacement D3 is zero with a tolerance of one millimeter in either direction. Optimally, the displacement D3 is zero with a tolerance of about one-quarter of a millimeter in either direction. Thereafter, the assembled band 112 and the liner 110 are inspected for material transfer blemishes. A microscope may be used to inspect the assembly.

Figure 24:
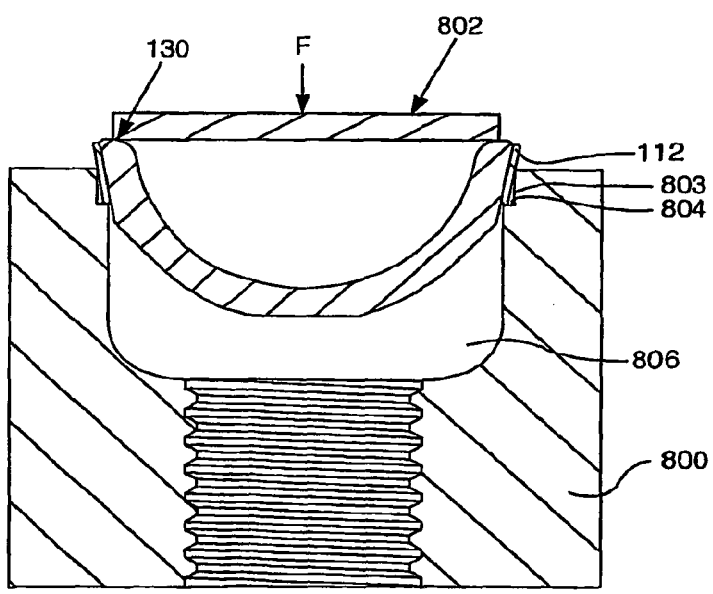
FIG. 24 is a sectional front view of a fixture for mounting a band to a liner in a second embodiment.

FIG. 24 illustrates a second embodiment of a fixture 800 for use in installing the band 112 on the liner 110. The fixture 800 includes a counter bore 803, a fixture face 804 and a well 806. To install the band 112 on the liner 110, the band 112 and the liner 110 are placed on the fixture 800 and a press (not shown) with a press platen 802 is used to press the band 112 on the liner 110. First, the fixture 800 is mounted to the press, which may be a computer numerically controlled press. Second, the press is set with a displacement rate, a minimum force, and a maximum force. The displacement rate may be from about 0.01 inch per minute to about 2.00 inches per minute maximum. In the depicted embodiment, the displacement rate is about 0.80 inches per minute to about 1.10 inches per minute maximum. The minimum force ranges from about 5000 pounds to 11000 pounds. In the depicted embodiment, the minimum force is about 8000 pounds. The maximum force ranges from about 8000 pounds to about 15000 pounds. In the depicted embodiment, the maximum force is about 10000 pounds. Third, the band 112 is placed on the liner 110 by hand. Fourth, the band 112 and the liner 110 are placed on the fixture 800 with the liner 110 protruding into the well 806 and the band 112 resting in the counter bore 803 and on the fixture face 804. The counter bore 803 provides the advantage of self-centering the assembly over the well 806. Fifth, the press platen 802 is advanced until it makes contact with the face 130 of the liner 110. The initial preload force on the liner 110 may be from about zero pounds to about ten pounds. Sixth, the press platen 802 applies a force F on the liner 110 until a displacement D3 is achieved between the band 112 and the liner 110. The displacement D3 is zero with a tolerance of one millimeter in either direction. Optimally, the displacement D3 is zero with a tolerance of about one-quarter of a millimeter in either direction. Thereafter, the assembled band 112 and the liner 110 are inspected for material transfer blemishes. A microscope may be used to inspect the assembly.

In view of the foregoing, it will be seen that the several advantages of the invention are achieved and attained.

The embodiments were chosen and described in order to best explain the principles of the invention and its practical application to thereby enable others skilled in the art to best utilize the invention in various embodiments and with various modifications as are suited to the particular use contemplated.

As various modifications could be made in the constructions and methods herein described and illustrated without departing from the scope of the invention, it is intended that all matter contained in the foregoing description or shown in the accompanying drawings shall be interpreted as illustrative rather than limiting. For example, while the first groove and the second groove have been depicted as annular, those of ordinary skill in the art would understand that the grooves may be intermittently spaced about the inner surface of the shell and still achieve the same function. Thus, the breadth and scope of the present invention should not be limited by any of the above-described exemplary embodiments, but should be defined only in accordance with the following claims appended hereto and their equivalents.

What is claimed is:

1. An acetabular cup assembly, comprising:
   a. a shell, the shell having a generally hemispherical concave inner surface, an outer surface, a face, and an apex, said inner surface further comprising an inner wall, the inner surface forming a first groove recessed into the shell, a second groove recessed into the shell, and a protrusion protruding from the shell, the protrusion located between said first groove and said second groove, said second groove being closer to the apex of the shell, wherein the first groove and the second groove are located below the inner wall; and
   b. a liner adapted to fit within said inner surface of said shell, the liner comprising an inner portion and a generally convex outer portion, said outer portion including a first bump and a second bump, said second bump being closer to the apex of said generally convex outer surface;
   c. said first and second grooves in combination with said protrusion of said shell and said first and second bumps of said liner forming an interference fit between said shell and said liner such that the push-out force required to separate the shell from the liner is greater than the push-in force required to seat the liner in the shell.

2. The acetabular cup assembly of claim 1, wherein the first groove and the second groove are separated by a first distance, and said first distance ranges from about one millimeter to about twenty millimeters.

3. The acetabular cup assembly according to claim 1, wherein the liner is selected from the group consisting of cross-linked polyethylene and conventional polyethylene.

4. The acetabular cup assembly of claim 1, wherein the liner includes anti-rotation tabs and the shell includes at least one scallop.

5. The acetabular cup assembly of claim 1, wherein the shell includes an insertion tool hole.

6. The acetabular cup assembly of claim 1, wherein the inner surface of the shell is highly polished.

7. The acetabular cup assembly of claim 1, wherein inner wall has a taper.

8. The acetabular cup assembly of claim 1, the inner wall includes a surface enhancement.

9. The acetabular cup assembly of claim 1, wherein the surface enhancement is selected from the group consisting of an acme-type stair-step, a reverse stair-step, or a predetermined surface roughness.

10. The acetabular cup assembly of claim 1, wherein the liner is selected from the group consisting of a constrained liner, a neutral liner, an anteverted liner, a lipped bearing liner, and a lateralized bearing liner.

11. The acetabular cup assembly of claim 1, wherein a central axis extends through the apex, a line extends from where the inner surface meets the second groove to where the central axis meets a planar surface defined by a plane extending through the face of the shell, the central axis and the line defining an angle, and wherein the angle ranges from about ten degrees to about eighty degrees.

12. The acetabular cup assembly according to claim 11, wherein said angle ranges from about forty to about seventy degrees.

13. The acetabular cup assembly of claim 1, wherein the push-out force required to separate the shell from the liner must overcome friction provided by the first bump engaging the first groove in combination with second bump engaging both the protrusion and the second groove.

14. The acetabular cup assembly of claim 1, wherein the second bump only slightly interferes with the protrusion.

15. An acetabular cup assembly, comprising:
   a. a hemispherical shell, the shell having a generally concave inner surface, an outer surface, and an apex, said inner surface further comprising a tapered inner wall, the inner surface forming a first groove recessed into the shell, a second groove recessed into the shell, and a protrusion protruding from the shell, the protrusion located between said first groove and said second groove; and
   b. a liner adapted to fit within said inner surface of said shell, the liner comprising an inner portion and a generally convex outer portion, said outer portion including a first bump and a second bump, said second bump being closer to an apex of the generally convex outer surface;
   c. wherein the protrusion of the shell and the second bump of the liner are configured to provide an interference fit between the shell and the liner such that the push-out force required to separate the shell from the liner is greater than the push-in force required to seat the liner in the shell.

16. The acetabular cup assembly of claim 15, wherein the second bump only slightly interferes with the protrusion.

17. The acetabular cup assembly of claim 15, wherein the first groove and the second groove are located between the tapered inner wall and the apex of the generally concave inner surface.

18. The acetabular cup assembly of claim 15, wherein the second groove is closer to the apex of the generally concave inner surface than the first groove.

19. The acetabular cup assembly of claim 15, wherein the push-out force required to separate the shell from the liner must overcome friction provided by the first bump engaging the first groove in combination with second bump engaging both the protrusion and the second groove.

20. An acetabular cup assembly, comprising:
   a. a hemispherical shell, the shell having a generally concave inner surface, an outer surface, a face, and an apex, the inner surface forming a first groove recessed into the shell, a second groove recessed into the shell, and a protrusion protruding from the shell, the protrusion located between said first groove and said second groove, the first and second grooves located between the apex and the face, the second groove being located closer to the apex than the first groove; and
   b. a liner adapted to fit within said inner surface of said shell, the liner comprising an inner portion and a generally convex outer portion, said outer portion including a first bump and a second bump, said second bump being closer to an apex of the generally convex outer surface;
   c. wherein, in use, the second bump of the liner engages both the protrusion and the second groove of the shell.

* * * * *